(12) United States Patent
Douglas

(10) Patent No.: US 11,006,100 B1
(45) Date of Patent: May 11, 2021

(54) SMART GLASSES SYSTEM

(71) Applicant: Robert Edwin Douglas, Winter Park, FL (US)

(72) Inventor: Robert Edwin Douglas, Winter Park, FL (US)

(*) Notice: Subject to any disclaimer, the term of this patent is extended or adjusted under 35 U.S.C. 154(b) by 0 days.

(21) Appl. No.: 16/828,352

(22) Filed: Mar. 24, 2020

Related U.S. Application Data

(63) Continuation-in-part of application No. 15/949,202, filed on Apr. 10, 2018.
(60) Provisional application No. 62/813,509, filed on Mar. 4, 2019.

(51) Int. Cl.
| | |
|---|---|
| *H04N 13/344* | (2018.01) |
| *A61B 1/00* | (2006.01) |
| *G08B 21/02* | (2006.01) |
| *G08B 7/06* | (2006.01) |
| *A61B 34/20* | (2016.01) |
| *A61B 90/00* | (2016.01) |
| *A61B 90/50* | (2016.01) |
| *A61B 17/00* | (2006.01) |

(52) U.S. Cl.
CPC ....... *H04N 13/344* (2018.05); *A61B 1/00041* (2013.01); *A61B 1/00048* (2013.01); *A61B 1/00055* (2013.01); *A61B 34/20* (2016.02); *A61B 90/361* (2016.02); *G08B 7/06* (2013.01); *G08B 21/02* (2013.01); *A61B 2017/00115* (2013.01); *A61B 2017/00216* (2013.01); *A61B 2034/2055* (2016.02); *A61B 2034/2065* (2016.02); *A61B 2090/502* (2016.02)

(58) Field of Classification Search
None
See application file for complete search history.

(56) References Cited

U.S. PATENT DOCUMENTS

| | | | |
|---|---|---|---|
| 9,579,060 B1* | 2/2017 | Lisy | A61B 5/0533 |
| 2005/0068171 A1* | 3/2005 | Kelliher | G08B 21/0283 |
| | | | 340/539.22 |
| 2016/0342840 A1* | 11/2016 | Mullins | G02B 27/0172 |
| 2018/0136486 A1* | 5/2018 | Macnamara | A61B 3/14 |
| 2019/0107623 A1* | 4/2019 | Campbell | G01S 17/931 |
| 2019/0142520 A1* | 5/2019 | VanDyken | A61B 90/37 |
| | | | 606/1 |

* cited by examiner

*Primary Examiner* — Jwalant Amin

(57) ABSTRACT

A physician performing a physical examination can miss subtle abnormalities, such as alterations of respiratory rate or dangerous skin lesion. A surgeon performing surgery can miss small areas of bleeding or tumor implants. This invention comprises head display unit comprising sensors that gathers data and in real time analyzes the data for potential hazards and alerts the user of a potential hazardous scenario.

16 Claims, 38 Drawing Sheets

Medical images and computer generated 3D representation of surgical device

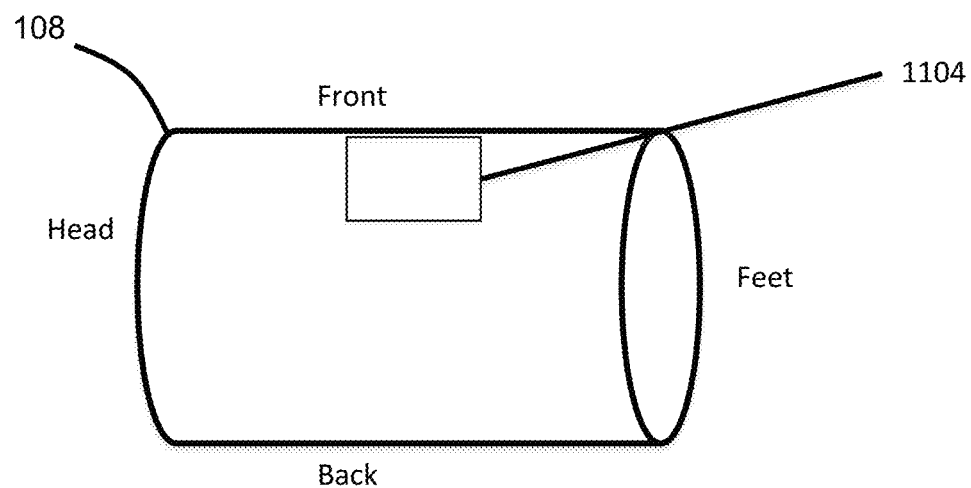
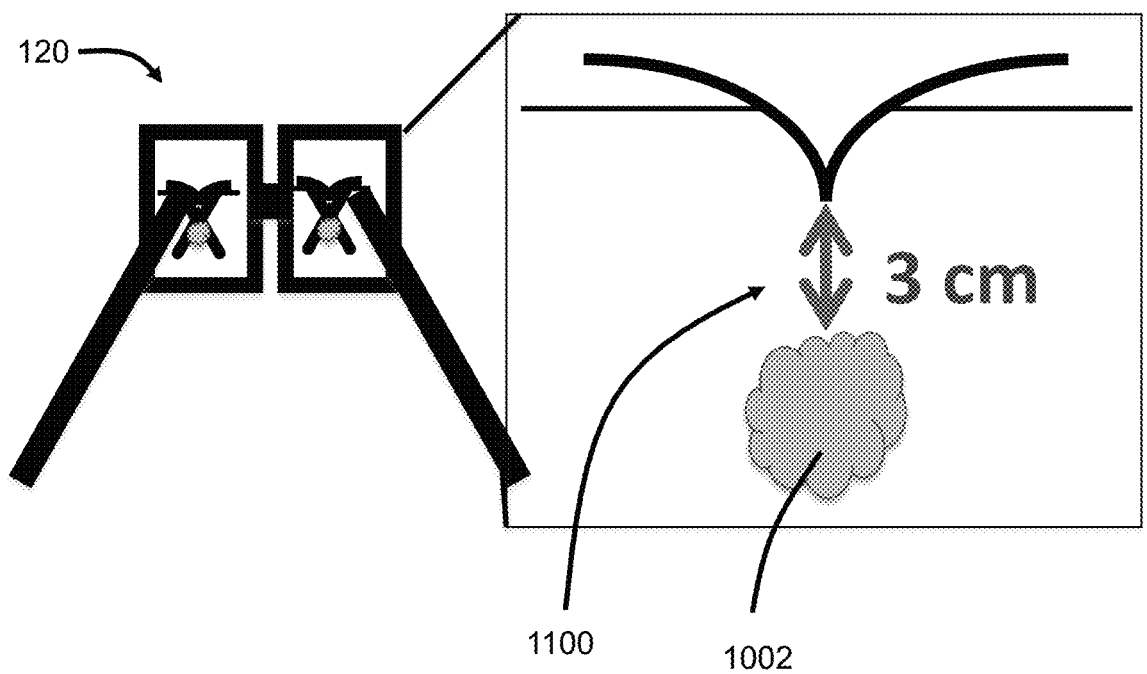
Figure 11

1002

1002

Figure 15A
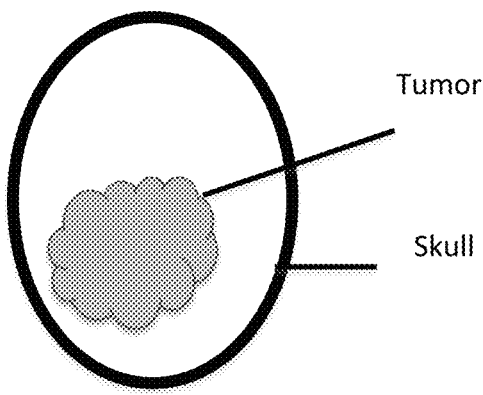
Tumor
Skull
Figure 15B
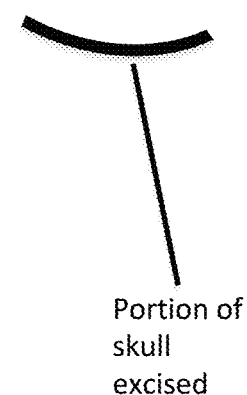
Portion of skull excised
Image estimate of craniotomy site
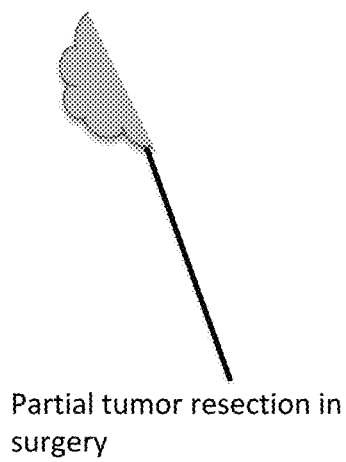
Partial tumor resection in surgery
Figure 15C
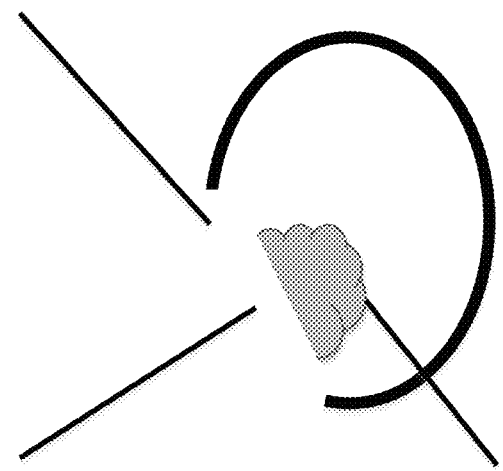
Image estimate of surgical cavity created by partial resection of tumor
Image estimate of residual tumor
Figure 15D Perform three-dimensional image wherein at least some of the voxels in the dataset have at least two data units (e.g., a MRI scan of the brain with a T1-weighted sequence and a T2-weighted sequence, a 4-phase CT scan of the liver, etc.)
2100

Display a three-dimensional image (e.g., stack of 2D slices, volume rendered image, MIP image, D3D image, etc.)
2101

Place volumetric 3D cursor into a three-dimensional image
2102

Use properties of the 3D cursor (e.g., boundaries of the 3D cursor, which separate the inside of the cursor from the outside of the cursor) to divide the three-dimensional image into at least two sub-volumes (e.g., sub-volume of voxels inside of the volume-subtending 3D cursor and sub-volume of voxels outside of the volume-subtending 3D cursor)
2103

Assign (e.g., via user input) at least one sub-volume a different dimension (e.g., a different phase, a different MRI sequence) from at least one other portion of the three-dimensional image
2104

2105
2106
2107

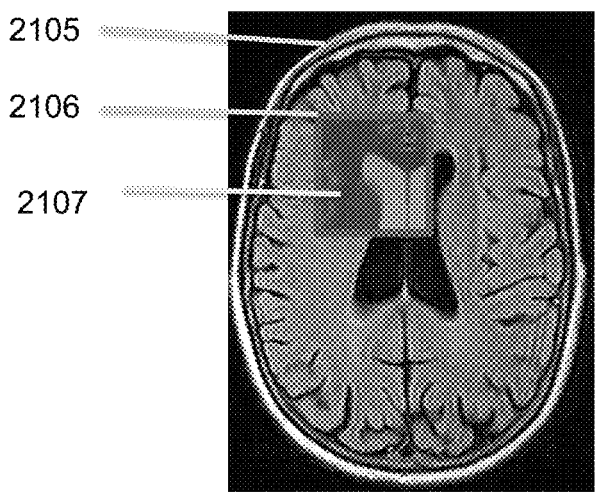

Figure 21

Step 1: The person wearing the SGS issues voice command "TV"
2400

Step 2: The L3TV cameras are activated by system control software
2401

Step 3: Imagery generated by the cameras is passed through the wireless element to the computer which reformats it, if required
2402

Step 4: Computer passes imagery data through wireless element to respective lenses for display
2403

Step 5: If voice command issues "zoom", then acoustics element passes signal through the wireless element to the computer
2404

Step 6: Computer recognizes the voice command and generates instructions to L3TV cameras to change fields-of-view (FOVs)
2405

Step 7: Instructions passed thru wireless element to L3TV cameras
2406

Step 8: Data generated by L3TV cameras goes thru above display process
2407

Step 9: When zoom is no longer needed the person wearing the SGS issues voice command "Normal" and SGS resume normal L3TV cameras imaging mode
2408

Figure 24

Step 1: The person wearing the SGS issues voice command "SA mode"
2500

Step 2: The LRF is activated by system control software and operates as described in 1, above
2501

Step 3: The L3TV cameras are activated by system control software and operates in 2, above
2502

Step 4: Acoustic signals received by the acoustic element are passed thru the wireless element to the computer
2503

Step 5: Computer analyzes acoustic data and applies detection algorithms for approaching/ receding/ stationary vehicles; generates messages accordingly; passes thru wireless element to display portion of lenses and acoustic transmit element
2504

Step 6: Given there is an approaching vehicle and the person wearing the SGS turns head, if needed, for the vehicle to be in FOV the person could place crosshair on vehicle and issue voice command "Range"
2505

Step 7: LRF provided range at specified intervals passes to computer via wireless element. Computer determines range rate changes and calculates time of arrival generates messages accordingly; passes thru wireless element to display portion of lenses and acoustic transmit element
2506

Step 8: Given the person wearing the SGS is at a crosswalk, they may invoke zoom command
2507

Figure 25

Step 1: The person wearing the SGS issues voice command "Calibrate"
2600

Step 2: The LRF is activated by system control software and operates as described in 1, above; laser pointer with colored dot is activated
2601

Step 3: The person wearing the SGS point system crosshair to some recognizable point (e.g., corner of door frame) and checks where the laser pointer dot is with respect the crosshair.
2602

Step 4: LRF adjusted, as needed to cause laser dot to coincide with center of crosshair.
2603

Figure 26

Generate a predetermined list of adverse event scenarios
3600

Establish a set of criteria for each sensor system that is predictive of an adverse event scenario
3601

Perform continuous analysis of the data gathered from the sensors on the HDU to determine if the set of criteria for each sensor system that is predictive of an adverse event scenario is met
3602

When the set of criteria for each sensor system that is predictive of an adverse event scenario is met provide an alert to the user via at least one of the group of:
- a visual alert wherein the HDU causes a first image of a volume of interest to be displayed on the left eye display and cause a second image of the volume of interest to be displayed on the right eye display, wherein the first image is aligned with a left eye of a user, and wherein the second image is aligned with a right eye of the user; and
- an audio alert from the set of speakers.
3603

Figure 36

Generate a predetermined list of adverse event scenarios
3700

Generate a database of sensor data of scenarios known to be adverse
3701

Generate a database of sensor data of scenarios known not to be adverse
3702

Gather sensor data from a head display unit (HDU)
3703

Perform artificial intelligence in real time to classify the sensor data as predictive of an adverse event scenario or not predictive of an adverse event scenario
3704

Alert a user wearing the HDU when the artificial intelligence algorithm predicts an adverse event scenario by a predetermined alert notification via at least one of the group of:
- a visual alert notification wherein the HDU causes a first image to be displayed on the left eye display and cause a second image of the volume of interest to be displayed on the right eye display, wherein the first image is aligned with a left eye of a user, and wherein the second image is aligned with a right eye of the user wherein the visual alert notification corresponds to the specific adverse event scenario;
- and an audio alert notification from at least one speaker wherein the auditory alert notification corresponds to the specific adverse event scenario.
3705

Figure 37

| Adverse Event Scenario | Visual alert notification | Audio alert notification |
|---|---|---|
| Melanoma on patient's right arm | Red circle surrounds melanoma | Voice recording states "melanoma on right arm" |
| Scalpel close to aorta | Red symbol at scalpel tip | "Danger proximitiy" |
| Falling asleep when driving | Brightest white flash | "Loud buzzing sound" |
| Step down | Mark edge of step with red line and show arrow pointing towards step | "Caution. Step down" |
| Stove left on | "Arrow pointing toward stove" | "Stove left on" |
| Wide receiver left open | "Arrow pointing towards open player" | "Wide receiver" |
| Pipe leaking | "Arrow points to leak" | "Leak identified" |

Figure 38

SMART GLASSES SYSTEM

TECHNICAL FIELD

Aspects of this disclosure are generally related to surgery, and more specifically the operating room setup and surgical devices.

BACKGROUND

The traditional operating room consists of personnel including the surgeon, anesthesiologist, nurses, and technicians, and equipment including the operating room table, bright lights, surgical instrumentation, supporting system equipment. Surgical instruments are directly manually controlled by the surgeon.

More recently, robotic surgical systems have been developed where the surgeon indirectly manually controls surgical instruments, such as cutting, cauterizing, suction, knot tying, etc., through robotic arms. Advantages may include smaller incisions, decreased blood loss, and shorter hospital stays. These techniques are gaining more acceptance in the operating room because of the advantages.

Stereotactic surgery is a technique for locating targets of surgical interest within the body relative to an external frame of reference using a 3D coordinate system. As an example, stereotactic neurosurgery has traditionally used a mechanical frame attached to the patient's skull or scalp, such that the head is in a fixed position within the coordinate system of the stereotactic device. In more recent techniques, patients undergo imaging exams (e.g., computed tomography (CT) scans) with a stereotactic frame or stereotactic markers placed onto reference points on either the skin or skull in place during the imaging examination. This establishes the patient's anatomy and the stereotactic reference points all within the same 3D coordinate system. Through stereotactic neurosurgery, precise localization can be performed, such as placement of a deep brain stimulator (DBS) leads placed through a small hole in the skull into a specific structure deep within the brain to treat Parkinson's Disease. In other surgeries, when the surgeon positions a probe inside the skull, the tip of the probe will register to a particular spot on the patient's image, which is helpful for surgical guidance.

Although the technological developments described above offer some advantages, there are several shortcomings associated with the modern day operating room and modern stereotactic surgical techniques. First, the 3D coordinate system only pertains to surgical devices that can be affixed to the frame. Free-standing objects separated from the stereotactic unit cannot be registered into the 3D coordinate system. Second, the 3D coordinate system only works for tissues that are immobile and non-deformable within the body (e.g., brain within rigid skull). Stereotactic system would not work for a mobile, deformable anatomic structure such as a breast; thus, precision procedures must be performed with constant image-guidance (e.g., MRI, CT, ultrasound) to account for the changing position and deformation of the breast tissue. Third, the volumetric 3D coordinate system of the patient's imaging study (e.g., MRI of a brain mass) is not manipulated in real time during the surgery in accordance with the expected ongoing surgical changes. As a result, there is a mismatch between the patient's surgical anatomy and the pre-operative imaging, which gets worse and worse as the surgical anatomy changes, such as removal of a glioma.

SUMMARY

All examples, aspects and features mentioned in this document can be combined in any technically possible way.

In accordance with an aspect an apparatus comprises a geo-registration and operating system within a hospital or clinic surgical setting to precisely locate points within the setting in an operating room coordinate system. Some implementations comprise, but are not limited to: precisely placed transmitters at 6 or more locations within the operating room. Some implementations further comprise transmitters in radio frequency (RF) or in the electro-magnetic (EM) spectrum. Some implementations further comprise transmitters could emit a unique signal within the frequency band or transmit in differing frequencies together with a schedule for transmission and a receiver for the transmitted signals coupled with a differential timing system to reflect the precise location within the operating room coordinate system of the receiver of any point within the operating room. Such a system would allow numerous objects to be registered into the same 3D coordinate system including both free standing objects and objects mounted to stereotactic devices, such as the following: operating room table; stereotactic markers on the patient's skin; stereotactic markers planted within the patient's tissues; key anatomical patient landmarks; surgeon's augmented reality headset; surgeon's cutting and dissecting device; surgical instruments; and, many types of surgical devices.

Some implementations of the geo-registration system a patient coordinate system is established wherein small (e.g., pin head size) pieces of material which will provide a distinct signature in a medical image (e.g., MRI, CT) are affixed to the patient. These pieces would be placed at locations on the body, which surround the area of a surgical procedure (i.e., at least 6 locations). Under this implementation, medical images would be obtained and 3D data generated and placed into a patient coordinate system and which geo-locates the pieces of material within the patient coordinate system.

Some implementations of the geo-registration system further comprise an external pointing system containing an inertial motion sensor which can be moved to and the tip of the pointer touch each of the pieces of material and the tip of which is thereby located within the patient coordinate system and a computational system within the pointing system which tracks the location of the tip of the pointer in relation to the patient 3D data and within the patient coordinate system.

Some implementations in connection with an operating room coordinate system further comprise registration of 3D patient data and associated patient coordinate system are geo-located with geo-registration system of the operating room (i.e., patient moved from medical imaging system to the operating room and the geo-location of each voxel of the patient 3D medical image is then converted to a geo-location within the operating room.) The receiver in the surgical setting could be moved to each of the pieces of material described in the patient coordinate system and the patient coordinate system then registered within the operating room geo-registration system.

Some implementations further comprise a pre-planning surgical process wherein the surgeon views the 3D volume containing the region for the operation and the pre-planning surgical process consists of, but not limited to: designating the volume of tissue on which the operation will be performed (e.g., tumor to be extracted); delineating the cutting surface within the region to access the designated volume of tissue for the operation; projecting the cutting surface to the external surface of the body from where the cutting will begin; taking note of and designating any areas for potential concern which are in close proximity to the cutting surface; obtaining metrics as of key elements of the surgery (e.g., depth of cut; proximity to arteries, veins, nerves); and recording the above for recall and display during the course of the operation.

Some implementations further comprise, in connection with the geo-registration and operating system a surgical device (e.g., but not limited to a scalpel with associated electronics) system with points along edge located with geo-registration system consisting of: if the conditions operating room coordinate system apply, then the surgical device would have a receiver for the transmitted signals coupled with a differential timing system to reflect the precise location of a precise point of the surgical device within the operating room; or if the patient coordinate system conditions apply, then the surgical device system would have the capability to compute the precise location of a precise point of the surgical device system within the patient coordinate system.

Some implementations further comprise the surgical device system would contain an inertial motion sensor which would measure roll, pitch and yaw of the surgical device and from that compute the precise location of the precise point of the surgical device, and the surgical device geometry (i.e., distance of the point of the surgical device from the precise point and also location of surgical device edge relative to precise point) compute the location of the various portions of the surgical device (e.g., point and edge) at any point in time within either operating room coordinate system or the patient coordinate system.

Some implementations further comprise a near real time communication system which transmits data from the surgical device system (i.e., key point on surgical device plus roll, pitch, and yaw) to the processor unit.

Some implementations further comprise a processing system which simultaneously computes surgical device location to include all cutting edges and its location within the patient 3D data.

Some implementations further comprise a near real time geo-locating system which tracks and records movements of the surgical device as it moves thru the patient and simultaneously through the patient 3D data.

Some implementations further comprise a head display system on/off (e.g., heads-up display which can be seen through when off and displays selected visual material when on) at direction of surgeon.

Some implementations further comprise a control system (e.g., audio from the surgeon or processor interface unit by surgeon's assistant) through which the surgeon can control what is to be displayed.

Some implementations further comprise at the start of the operation, the surgeon could select to display: patient with data considered relevant to surgeon (e.g., surgery type and objective; patient condition; the pre-planned cut line (length and planned depth) projected onto the patient; notes collected during the planning on any areas for potential concern which are in close proximity to the cutting surface).

Some implementations further comprise a process to compare the tracked movements of the surgical device with the planned cutting surface consisting of: a display of actual cutting surface vs. planned cutting surface on the surgeon's head display unit; metrics to inform the degree of variation of actual vs. planned; computation of needed angular approach (yaw, pitch and roll of cutting edge of surgical device) to arrive at the volume of tissue on which the operation will be performed; feedback to surgeon showing degree and direction of angular movements required to correct the variation of actual vs. planned cutting surface.

Some implementations further comprise deformable (e.g., breast, liver, brain, etc.) tissue (i.e., repositioning and/or resizing/reorienting of original voxels) within the patient 3D data to reflect pull back of tissue to access the designated volume of tissue for the operation as function of width of the pull back and depth of surgical cut and the type(s) of tissue involved.

Some implementations further comprise non-deformable (e.g., bone) tissue (i.e., repositioning/reorienting of voxels without resizing) within the patient 3D data to reflect movement of tissues to access the designated volume of tissue for the operation as a function of the surgical maneuver.

Some implementations further comprise of the placement of a surgical apparatus into the patient with the corresponding 3D representation of the surgical device being placed into the 3D patient imaging dataset.

Some implementations further comprise a process for color coding the deformable tissue to: reflect proximity of the cutting edge of the surgical device to volume of tissue on which the operation will be performed; or reflect distance to any areas of potential concern which are in close proximity to the cutting surface.

Some implementations further comprise an application of a variable degree of transparency of deformable tissue to enable viewing organs in proximity to the surgical cut.

Some implementations further comprise a display of metrics during the course of the operation to: show distances from cut to designated volume of tissue for the operation; show distances to areas of potential concern which are in close proximity to the cutting surface; and key organs and to surgical target for operation.

Some implementations further comprise isolation of the tissue intended for the operation and present in 3D to the surgeon during planning for and conduct of an operation which would include, but not limited to the following anatomical sites: brain; head and neck structures; chest; abdomen; pelvis; and, extremities.

Some implementations further comprise for a tumor type of operation, encapsulate the tissue for the operation and some additional margin of tissue to ensure all tissue of concern has been retrieved.

Some implementations further comprise performing segmentation on the encapsulated tissue to distinguish between tissue of concern and benign tissue (per U.S. patent application Ser. No. 15/904,092). Some implementations further comprise removing benign tissue leaving only tissue of concern. Some implementations further comprise determining points, within the 3D data set containing the tissue of concern, those points closest to the left eye viewing point and those closest to the right eye viewing point (note this results in a convex surface point toward the surgeon). This could be replicated from multiple angles, resulting in a 3D volume which represents the outer surface of the tissue of concern. Some implementations further comprise, at the direction of the surgeon, performing a smoothing operation on the above volume to remove artifacts in the volume. Some implementations further comprise displaying the volume on the surgeon's head mounted display (HMD) together with metrics to show the size of this tissue.

Some implementations further comprise for a heart type of operation using the 3D data set, separate the heart into two pieces such that the internal structure within the heart can be viewed in 3D with the surgeon's HMD. Some implementations further comprise, using metrics, calculation of the volumes of the left and right atriums and left and right ventricles. Some implementations further comprise encapsulation of each of the heart valves for 3D display on surgeon's HMD; and, as required, use segmentation to remove extraneous tissue.

Some implementations further comprise a process to generate a real time medical imaging dataset. The starting point for such a dataset is the patient's pre-operative images. As the surgery progresses, the medical imaging dataset will be updated. As an example, as tissues are removed, they can be analyzed (e.g., size, shape, weight) and the surgical cavity can be analyzed (e.g., measure cavity by laser range finder to generate 3D map of the surgical cavity). A corresponding volume of the 3D medical imaging dataset will be removed, such that the medical imaging data is updated. Alternatively, hardware can be added into the operating bed. A corresponding digital 3D representation of the surgical device will be inserted into the medical images with voxels manipulated accordingly to account for the new volume. The resultant volume will represent a working copy of the estimated 3D medical imaging dataset and will be available to the surgeon in real time.

Some implementations further comprise a process for stacking imaging slices to generate a movable volume, which can be then filtered, segmented and rendered.

Some implementations further comprise a process for generating a 4D cursor, with the dimensions comprising length, width, height and time.

Some implementations further comprise a process for generating a multi-dimensional (5D or higher) cursor, which would include length, width, time, and tissue property(ies).

Some implementations further comprise a recording of surgical device and its cutting-edge locations in conjunction with the patient 3D data during the course of the operation.

In accordance with an aspect an apparatus comprises: a plurality of spatial locators adapted to be used in an operating room; a medical image registration device configured to use information from the spatial locators to register at least one medical image with respect to a human body in the operating room that will undergo a surgical procedure; and a display that presents the registered medical image.

In accordance with an aspect a method comprises: receiving data from a plurality of spatial locators adapted to be used in an operating room; using the data from the spatial locators to register at least one medical image with respect to a human body in the operating room that will undergo a surgical procedure; and presenting the registered medical image on a display.

In some embodiments, a smart glasses system is incorporated. In some implementations, mounted on the eye glasses will include a scanning laser range finder (LRF) to determine range and elevation to points ahead along one's path. In some implementations, there will be attached to the eye glasses two low light level TV (L3TV) cameras whose generated video sequence will be presented on the lenses. In some implementations there will be attached to the eye glasses two thermal sights (i.e., Forward Looking Infrared (FLIR)). In some implementations, mounted on the eye glasses will include an audio transmit/receive device(s). The device will transmit audio warnings, system status, and external information received. The device will receive commands from the person wearing the glasses and other sounds which may be of interest or concern. In some implementations, mounted on the eye glasses will include an inclinometer (or inertial measurement unit (IMU)) to indicate the vertical angle of the eye glasses (or roll, pitch and yaw of the eye glasses). In some implementations, mounted on the eye glasses will include a wireless transmit/receive element. The wireless element will transmit data from the LRF, L3TV or FLIR cameras, and inclinometers/IMU. The wireless element will receive data from the compute element which will subsequently be passed to the lenses and/or audio elements. In some implementations, mounted on the eye glasses will include a battery to supply power to the afore-mentioned elements. In some implementations, mounted on the eye glasses or compute element will include an operating room coordinate. In some implementations, mounted on the eye glasses or compute element will include a global positioning system (GPS) to provide the coordinates of the person's location. In some implementations, mounted on the person (e.g., belt) wearing the eye glasses will include a computing element and associated battery pack. The computer will process the algorithms that integrate and process sensor data (i.e., LRF, inclinometer/IMU, L3TV cameras, audio receive element, and GPS) and from this generate displays for the eye glasses lenses and audio transmit. The computer will store information such as, but not limited to previously generated scenes, maps, etc.

The preferred embodiment is for such glasses to be used in the operating room to improve a surgeon's understanding of the patient's anatomy. The smart glasses system includes, but is not limited to the following: a set of see thru lenses with augmented reality (AR) overlay; a computational element; an auditory signal receipt/generation element; a scanning element (e.g., LIDAR or laser range finder); an inclinometer; a spatial locator system (e.g., described above or via a GPS type system); a low light level TV camera; a wireless link (transmit/receive between glasses and compute element); a wireless link to other data types (e.g., patient information, etc.); and, a software component. The software component includes, but is not limited to the following: a voice command recognition; an obstacle detection; a scene analysis (e.g., anatomic feature recognition, etc.); sound analysis (e.g., telltale noises from surgical tools, etc.).

The software component includes artificial intelligence/AR generation, to perform analysis of the following: distance to obstacles; highlight obstacles along surgical dissection path (e.g., draw red circle around); draw line for guidance on dissection path; anatomy recognition; next steps surgically; approaching danger analysis (e.g., task coordination between surgeons); map/floor plan storage; route generation. This system would have a wide range of features for functionality, which include, but is not limited to, the following: issues verbal commands to invoke desired elements of system functions; enhanced brightness for dark areas (e.g., sometimes the surgical anatomy of interest is in the shadow); display on glasses results of AFAR (e.g., distance to obstacles, highlight obstacles along path (e.g., draw red circle around), picture in picture of selected type objects (e.g., crosswalk signs), and present maps/floor plans with person's location and direction facing/moving). Surgical errors can occur due to a lack of situational awareness—an example being a pedestrian entering a crosswalk and being hit by an approaching vehicle. In accordance with an aspect an apparatus comprises: eye glasses with see through lenses which are also capable of displaying computer generated symbology to be superimposed on the visual scene. In some implementations, mounted on the eye glasses will include a scanning laser range finder (LRF) to determine range and elevation to points in the surgical cavity.

In some implementations, a LIDAR/LRF is placed on an endoscopy-type device (or the like, such as bronchoscopy, laparoscopy, etc.) wherein the surface of a structure inside of the human body can be mapped precisely and thereby aid surgical operations. The preferred embodiment would be to have a rapid scanning of the surgical cavity to generate a real-time map, which would have value to the surgeon. Such a situation would integrate with techniques described in this patent and techniques described in U.S. patent application Ser. No. 16/509,592, Implantable markers to aid surgical operations.

Some of the techniques in this patent are performed by utilizing techniques described in: U.S. patent application Ser. No. 15/878,463, Interactive 3D cursor for use in medical imaging; U.S. patent application Ser. No. 16/010,925, Interactive placement of a 3D digital representation of a surgical device or anatomic feature into a 3D radiologic image for pre-operative planning; U.S. patent application Ser. No. 15/904,092, Processing 3D medical images to enhance visualization; U.S. patent application Ser. No. 15/949,202, Smart operating room equipped with smart surgical devices; U.S. Pat. No. 9,473,766, Method and apparatus for three dimensional viewing of images; U.S. Pat. No. 9,615,806, Method and apparatus for creation and display of artifact corrected three dimensional (3D) volumetric data from biplane fluoroscopic image acquisition; U.S. patent Ser. No. 14/644,489, Method and apparatus for creation and display of artifact corrected three dimensional (3D) volumetric data from biplane fluoroscopic image acquisition; U.S. Pat. No. 9,980,691, Method and apparatus for three dimensional viewing of images; U.S. Pat. No. 9,349,183, Method and apparatus for three dimensional viewing of images; U.S. patent application Ser. No. 16/195,251, Interactive voxel manipulation in volumetric medical imaging for virtual motion, deformable tissue, and virtual radiological dissection; U.S. patent application Ser. No. 16/509,592, Implantable markers to aid surgical operations; U.S. patent application Ser. No. 16/524,275, Using geo-registered tools to manipulate three-dimensional medical images; PCT/US19/478, A virtual tool kit for radiologists; U.S. patent application Ser. No. 16/563,985, A method and apparatus for the interaction of virtual tools and geo-registered tools; U.S. patent application Ser. No. 16/594,139, Method and apparatus for performing 3D imaging examinations of a structure under different configurations and analyzing morphologic changes; U.S. patent application Ser. No. 16/683,256, Method and apparatus for performing 3D imaging examinations of a structure under different configurations and analyzing morphologic changes; U.S. patent application Ser. No. 16/703,629, Radiologist-assisted machine learning with volume-subtending 3D cursor; PCT/US19/239, Radiologist-assisted machine learning with interactive, volume-subtending 3D cursor; U.S. provisional application No. 62/843,612, A method of creating a computer-generated patient specific image; U.S. provisional application No. 62/846,770, A method of prioritized volume rendering to improve visualization of prioritized items within a 3D volume; U.S. provisional application No. 62/850,002, A method of creating an artificial intelligence generated differential diagnosis and management recommendation tool boxes during medical personnel analysis and reporting; U.S. patent application Ser. No. 16/654,047, A method to modify imaging protocols in real time through implementation of artificial intelligence; U.S. provisional application No. 62/856,185, A method of image manipulation based on eye tracking; U.S. patent application Ser. No. 16/506,073, A method for illustrating direction of blood flow via pointers; U.S. patent application No. 62/906,125, A method and apparatus for stereoscopic rendering of mobile fluids; and, U.S. patent application No. 62/939,685, Method and apparatus for development of an organ-specific coordinate system.

In some embodiments, a smart glasses system is incorporated for surgical applications. Specifically, the surgeon would wear the smart glasses during the surgery, which could help guide landmarks including distance to target and surgical steps. The smart glasses system includes, but is not limited to the following: a set of see thru lenses with augmented reality (AR) overlay; a computational element; an auditory signal receipt/generation element; a scanning element (e.g., LIDAR or laser range finder); an inclinometer; a spatial locator system (e.g., described above or via a GPS type system); a low light level TV camera; a wireless link (transmit/receive between glasses and compute element); a wireless link to other data types (e.g., internet, radio, weather, temperature, music, news, etc.); and, a software component.

In some embodiments, a smart glasses system is incorporated for non-medical applications. The software component includes, but is not limited to the following: a voice command recognition; an obstacle detection; a scene analysis (e.g., anatomic, facial recognition, crosswalks signs recognition, etc.); sound analysis (e.g., incoming car, etc.). The software component includes artificial intelligence/AR generation, to perform analysis of the following: distance to obstacles; highlight obstacles along path (e.g., draw red circle around); draw line for stairs/sidewalk irregularities/curbs; animal recognition; person/facial recognition; approaching vehicles; text generation for audio sounds; approaching danger analysis (e.g., by sound detect approaching car—display warning message); map/floor plan storage; route generation. This system would have a wide range of features for functionality, which include, but is not limited to, the following: issues verbal commands to invoke desired elements of system functions; enhanced brightness for dark areas; display on glasses results of AI/AR (e.g., distance to obstacles, highlight obstacles along path (e.g., draw red circle around), draw line for stairs/sidewalk irregularities/curbs, animal recognition, person/facial recognition, approaching vehicles, text generation for audio sounds, warning for obstacles (audio, draw lines, measure distances, etc.), picture in picture of selected type objects (e.g., crosswalk signs), and present maps/floor plans with person's location and direction facing/moving). Thus, in addition to enhancing surgical capabilities, this method and apparatus can be used to inter alia help the visually impaired. The system could also be used by athletes to extend workout periods to time periods of low light level. There are a large number of accidents which involve tripping and falling. This can occur through inattention, visual impairment, or low light level. Other accidents occur due to a lack of situational awareness—an example being a pedestrian entering a crosswalk and being hit by an approaching vehicle. Some of these accidents are minor, however, others can be very painful and/or costly. As the baby boomer generation ages, one can expect the frequency of accidents will increase for that generation in particular.

In accordance with an aspect a method comprises: presentation onto the lenses of eye glasses warning symbols to alert the person wearing the glasses of conditions which may be hazardous to their health. Examples include, but are not limited to approaching stairs, curbs, obstacles in one's path and low light level. In some implementations, the warning could be presented with an auditory presentation or in combination with the visual presentation. In further aspects of this method comprises: assessment of an impending situation which could be dangerous and presentation onto the lenses of eye glasses warning symbols to alert the person wearing the glasses of a potentially hazardous situation. An example includes but is not limited to a person approaching a crosswalk as a vehicle is approaching. In some implementations, the warning could be presented auditorily or in combination with the visual presentation. In some implementations, test could be displayed of person speaking. This aspect could be used in conjunction with translation software for foreign languages. In some implementations, the system could be used in conjunction with facial recognition software. Given a person's face was recognized, the name could be displayed visually and/or auditory.

In accordance with an aspect a process comprises: determination of distances and elevation (or elevation changes) along one's path based upon: LRF range; the height above ground level of the eye glasses; and inclinometer angle/IMU roll, pitch, yaw data; from this, generate symbology to be displayed and location within the eye glasses lenses (i.e., which specific pixels) to display the symbology; and generating messages to be transmitted by the wireless element. In accordance with an aspect a further process comprises registration of the location of the eye glasses (i.e., height above ground level, location and look angle within home or area). In accordance with an aspect a further process comprises receipt of voice commands from the person wearing the eye glasses and changing the system mode accordingly. Examples include but are not limited to: on/off; turn on/off L3TV or FLIR cameras; increase sound level of auditory system.

In accordance with an aspect software comprises a set of algorithms to operate the above methods and process above based on the data received from the sensing elements. Additionally, the software will monitor the health and maintenance of the overall system and generate display of status items.

With the L3TV cameras in the turned-on mode, record 'normal' for one's daily path. For example, as one enters the kitchen, the bedroom, etc. Then during daily activity, invoke the 'compare' during which current scene is registered with the 'normal' scene and differences highlighted. One display option would be to subtract the 'normal' from the current and show only what is different.

Another mode of the SGS functioning to improve situational awareness is as follows. When the person wearing the SGS approaches situations that could potentially be hazardous such as crosswalk at a road intersection, the receive portion of the acoustic could provide warning messages of approaching vehicles. The warning could be shown on the SGS display lenses and/or acoustic. The L3TV cameras could monitor and zoom in on the pedestrian signals indicating walk/countdown/wait.

Another mode of SGS functioning to assist the person wearing the SGS with daily activities. The SGS could assist persons who have difficulty in understanding the spoken word of another person by invoking speech recognition software in conjunction with audio receive element to pass the detected speech and pass to the computer which would apply the speech recognition software and sent to the display the recognized words via the wireless system. Note that this mode would also support foreign word translation. This assist function could also include facial recognition (or animal recognition) software. The scene captured by the L3TV cameras would be sent through the wireless element to the computer which would run the facial recognition software, identify the person in the scene and pass the name through the wireless element to the display. An audio of the person's name could also be transmitted.

One mode of the SGS functioning is to initialize/calibrate as follows. The SGS is responsive to voice commands such as "initialize" at which time the system would direct actions for the person to take to proper calibration of the system with respect to where the system is pointing. The LRF could have a coincident laser pointer-beam transmitting a colored (e.g., red) dot. A crosshair could be displayed on the display portion of the SGS lenses. The person's head could be turned to distinguishable location (e.g., corner of door frame) and the LRF (with scanning mode turned off) look angle adjusted such that the laser pointer colored dot coincided with the crosshair. Modes of the SGS could be changed at the voice command of the person wearing the system.

Some embodiments comprise a head display unit (HDU) comprising a processor, a set of sensors including a head tracking device, an eye tracking device, an audio recording device, a lidar device, and a forward looking camera, a left eye display, a right eye display, a set of speakers, a non-transitory memory having computer-executable instructions stored thereupon which, when executed by the processor of the head display unit, cause the HDU to generate a predetermined list of adverse event scenarios, establish a set of criteria for each sensor system that is predictive of an adverse event scenario, perform continuous analysis of the data gathered from the sensors on the HDU to determine if the set of criteria for each sensor system that is predictive of an adverse event scenario is met, and when the set of criteria for each sensor system that is predictive of an adverse event scenario is met provide an alert to the user via at least one of the group of a visual alert wherein the HDU causes a first image of a volume of interest to be displayed on the left eye display and cause a second image of the volume of interest to be displayed on the right eye display, wherein the first image is aligned with a left eye of a user, and wherein the second image is aligned with a right eye of the user and an audio alert from the set of speakers. Some embodiments comprise wherein the adverse event scenario includes a dangerous physical examination finding of a patient. For example, a skin lesion on a patient may go unnoticed and represent an adverse event. Some embodiments comprise wherein the adverse event scenario includes a dangerous observation during surgery. For example, active bleeding may be present during the surgery, but go unnoticed during surgery. Some embodiments comprise wherein the adverse event scenario includes a dangerous event during driving. For example, a pedestrian may be crossing the highway in front of fast moving traffic. Alternatively, a driver may be drifting off to sleep and the driver's head falls downward, which could be detected by the IMU sensor. Some embodiments comprise wherein the adverse event scenario includes dangerous events during walking. For example, a user may be crossing the crosswalk when the walk sign is on, but a car could be running the red light. Some embodiments comprise wherein the adverse event scenario includes dangerous events that can occur in the household. For example, a user may be cooking, but forget to turn off the stove. Alternatively, the user may be prescribed to walk every hour by their to avoid blood clots, but forget to get up and walk. Alternatively, it could be walking down a steep set of stairs. Some embodiments comprise wherein the adverse event scenario includes sports events. For example, a user may be about to take a golf shot near a tree root, which could interfere with a swing. Alternatively, the person could be running over hurdles, catching a pop fly or throwing a football. Some embodiments comprise wherein the adverse event scenario includes occupation related. For example, a user may be about to perform work on an electrical box and about to touch a live wire. Alternatively, it could be a plumber working under the sink looking for a leak.

Some embodiments comprise a laser range finder is in communication with a sensing orientation system and also in communication with a computing system to determine distances in front of the direction the person wearing the SGS and determine elevation changes in front of the direction the person wearing the SGS is viewing.

Some embodiments comprise a SGS wherein a see-through eye glass system with transparent display is in communication with a computing system to display distances in front of the direction the person wearing the SGS is viewing.

Some embodiments comprise a SGS wherein a see-through eye glass system with transparent display is in communication with a computing system to display elevation changes in front of the direction the person (wearing apparatus (claim 8) is viewing. Note that the person wearing these see-through eye glass system with transparent display would see the scene before them as per normal but the symbols would be superimposed onto the scene in the area of concern as view from the person's perspective along with a visible and/or auditory message.

Some embodiments comprise a see-through eye glass system with transparent display (except for symbols and letters) is in communication with a computing system to display a scene, previously digitally recorded, from the same position, and viewing angle. Alternatively, display the current scene of the area as it is now and being observed by the person SGS. Alternatively, perform scene subtraction the scenes and display changed/new/repositioned items. Note that the person wearing the SGS would see the scene before them as per normal but the symbols would be superimposed onto the scene in the area of concern as view from the person's perspective along with a visible and/or auditory message.

Some embodiments comprise an SGS in communication with a computing system to display the current scene as it is now and being observed by the person wearing the SGS equipped with the L3TV. The L3TV can digitally brighten the scene being displayed, digitally zoom in on the center of scene being displayed. Note that the person wearing the SGS would see the scene before them as per normal but the symbols would be superimposed onto the scene in the area of concern as view from the person's perspective along with a visible and/or auditory message.

Some embodiments comprise a method wherein the SGS can with transparent display and auditory receive element is in communication with a computing system to provide situational awareness based on inclusion of analysis of auditory input from sounds emitted externally (or internally of the field of view). Some embodiments display a warning as per analysis. Note that the person wearing the SGS would see the scene before them as per normal but the symbols would be superimposed onto the scene in the area of concern as view from the person's perspective along with a visible and/or auditory message.

Some embodiments comprise an apparatus comprising: a see-through eye glass system with one or more of the following: transparent display (except for symbols and letters); an auditory transmit and receive element; a laser range finder; two low light level TV or FLIR cameras; an orientation sensor—inclinometer/inertial measurement system; a global positioning system; a wireless digital transmission and receive communication system; a battery/power system in eye glasses frame, and, a computing system with power package and wireless transmit/receive element. The software with modules comprises system set-up and start up instructions. A laser range finder computes distance and elevation changes from reference point on person (e.g., eyes). The eye glass displays: warning messages; symbols; and scene/subtracted scene. Additional features include: auditory messages, situational analysis, calibration, health and maintenance.

Some embodiments comprise a method of alerting a user of a hazardous scenario comprising: generating a predetermined list of adverse event scenarios; generating a database of sensor data of scenarios known to be adverse; generating a database of sensor data of scenarios known not to be adverse; gathering sensor data from a head display unit (HDU); performing artificial intelligence in real time to classify the sensor data as predictive of an adverse event scenario or not predictive of an adverse event scenario; and alerting a user wearing the HDU when the artificial intelligence algorithm predicts an adverse event scenario by a predetermined alert notification via at least one of the group of: a visual alert notification wherein the HDU causes a first image to be displayed on the left eye display and cause a second image of the volume of interest to be displayed on the right eye display, wherein the first image is aligned with a left eye of a user, and wherein the second image is aligned with a right eye of the user wherein the visual alert notification corresponds to the specific adverse event scenario; and an audio alert notification from at least one speaker wherein the auditory alert notification corresponds to the specific adverse event scenario.

Some embodiments comprise and apparatus comprising: an endoscopy probe; and a lidar sensor. Some embodiments comprise wherein the lidar sensor generates a voxelated dataset from the inside of a patient's body during endoscopic surgery. For example, the lidar sensor could generate a voxelated dataset of the inside of the trachea during a bronchoscopy examination. Some embodiments comprise wherein the voxelated lidar dataset is registered to a cross-sectional imaging examination voxelated dataset. For example, the voxelated dataset of the inside of the trachea during a bronchoscopy examination can be registered to the trachea from a voxelated dataset from a chest CT examination. Some embodiments comprise wherein a surgeon uses the co-registered voxelated dataset for surgical navigation. For example, a tumor could be marked on the CT scan and the real time voxelated dataset from the lidar sensor co-registered to the CT scan could be used as navigation. For example, the distance to the tumor could be marked.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 11 illustrates metrics available during an operation, such as depth of cut, as seen through the surgeon's augmented reality headset.

FIG. 21 illustrates a method to use a multi-dimensional cursor.

FIG. 24 is a flow chart of the system in L3TV camera mode.

FIG. 25 is a flow chart of the system in the SGS situational awareness mode.

FIG. 26 is a flow chart of the system in initialize/calibrate mode.

FIG. 33B illustrates what picture a person sees when the L3TV camera is on.

FIG. 36 illustrates a flow diagram wherein the user is alerted of an adverse scenario.

FIG. 37 illustrates a flow diagram for a method to alert a user of a hazardous scenario.

FIG. 38 illustrates a table of programmed visual alert notifications and auditory alert notifications to correspond to adverse event scenarios.

DETAILED DESCRIPTION

Some aspects, features and implementations described herein may include machines such as computers, electronic components, optical components, and processes such as computer-implemented steps. It will be apparent to those of ordinary skill in the art that the computer-implemented steps may be stored as computer-executable instructions on a non-transitory computer-readable medium. Furthermore, it will be understood by those of ordinary skill in the art that the computer-executable instructions may be executed on a variety of tangible processor devices. For ease of exposition, not every step, device or component that may be part of a computer or data storage system is described herein. Those of ordinary skill in the art will recognize such steps, devices and components in view of the teachings of the present disclosure and the knowledge generally available to those of ordinary skill in the art. The corresponding machines and processes are therefore enabled and within the scope of the disclosure.

Figure 1:
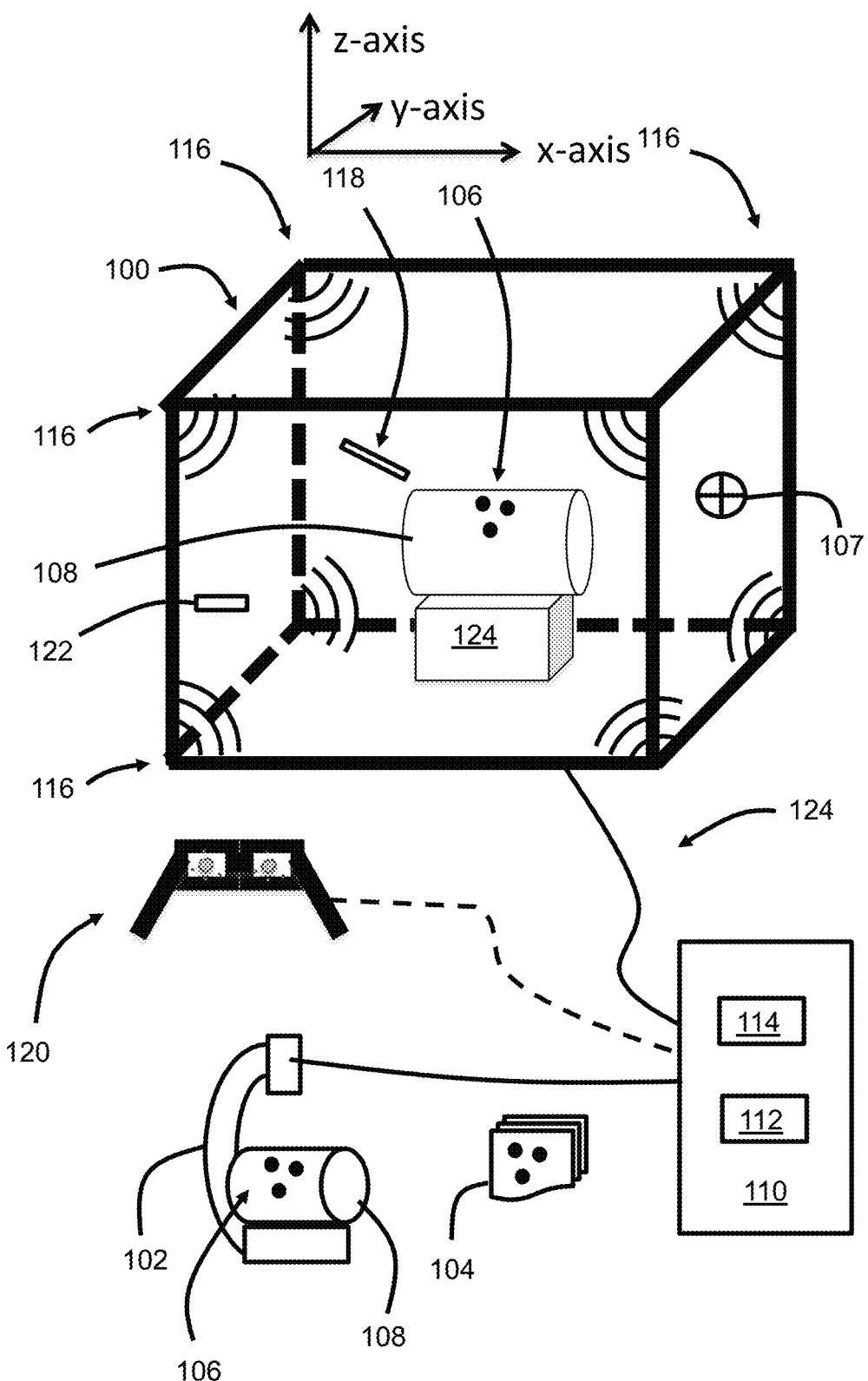
FIG. 1 illustrates an intelligent operating room in accordance with some aspects of the invention.

FIG. 1 illustrates an intelligent operating room 100 in accordance with some aspects of the invention. Aspects of an operation including interactions between components such as a surgical device (SD) 118 and a patient 108 are planned, monitored, and facilitated using a medical image registration computer 110. The computer uses data from spatial locators in the intelligent operating room to calculate the spatial location and orientation of the surgical device 118, both within the patient 108 and within a patient 3D data set 114 that includes a virtual representation of the patient. The 3D data set is registered with respect to the surgical device and the body of the patient. Virtual images of completed and planned surgical procedures are generated to enhance the surgeon's visualization of the progress of the operation. The virtual images can be displayed, on the command of the surgeon, on a HDU (head display unit) 120, e.g. an augmented reality headset. For example, the virtual images may be superimposed on the surgeon's real-world view with coordinated alignment such that virtual aspects of the operation can be viewed in their real-world locations and orientations from any distance and angle.

A radiological imaging instrument 102 is used to obtain medical images 104 prior to the operation. Reference point markers 106, which are readily recognizable in the medical images 104, are placed on the patient 108 prior to taking the images. The reference points would typically be proximate to, or surround, the locus of the operation, and may be placed on surfaces with little anticipated movement. The medical images 104, which may include multiple 2D slices, are provided to the computer 110. The computer may include processors, memory, non-volatile storage, and a control elements program 112 for processing the medical images 104 to help generate the patent 3D data set and perform other functions that will be described below.

The surgeon performs a pre-surgery planning process which may include a thorough review of the: patient data; objectives of the prospective operation; planning the operation cut(s); and delineation the cut parameters (e.g., cut location; depth); designation of areas of concern; device(s) to be placed; and a digital shape (e.g., sphere) around the tissue to be operated on. These plans are then entered into the patient 3D data set 114 and saved as a pre-surgical planning file on the computer 110.

The patient 108 is transported from the radiology room to the intelligent operating room 100 in preparation for surgery. The gurney 124 with the patient may be aligned with the long side of a rectangular room. Both the patient 108 and surgical device are spatially registered with respect to the patient 3D data set 114. Spatial location within the intelligent operating room may be based on one or both of inertial motion sensors and the time-of-flight of signals transmitted between transmitter/receiver pairs. In one example the difference between transmission and receipt of signals 116 emitted by transmitters precisely located within the operating room and receivers located in or on the patient and/or surgical device 118 are used to calculate distances, each of which defines a sphere, and multiple spheres are used to calculate precise spatial locations within the operating room. In another example a pointer 122 with an inertial motion sensor is used to spatially locate patient and/or surgical device reference points with respect to at least one fixed registration point 107 in the intelligent operating room. For example, the pointer 122 may be placed in contact with the registration point 107 and then placed in contact with one of the reference point markers 106 on the patient, and then the inertial motion data may be used to calculate the location of the reference point marker with respect to the registration point. Similarly, the inertial motion sensor equipped surgical device could be initialized by being placed in contact with the registration point. Utilizing both inertial motion sensing data and receiver/transmitter pair distance data may provide even more precise and reliable spatial location. The raw spatial location data may be converted to an X, Y, Z location in the operating room coordinate system. Spatially locating each of the reference points, e.g. at differing orientations/pointing positions and directions of point, establishes a patient coordinate system.

As will be explained in greater detail below, at the start of the operation the surgeon can prompt display of the planned cut in an image superimposed on the patient 108, together with notes prepared during the pre-planning process. Furthermore, the planned cut can be displayed in the surgeon's augmented reality headset 120, providing stereoscopic imaging since the headsets provide unique images to each eye. In one implementation the images are displayed in accordance with U.S. Pat. No. 8,384,771, which is incorporated by reference. During the operation, progress can be displayed both in metrics with respect to distance of the cut from the tissues to be operated on and distances to areas of concern. Also, if the surface of the actual cut varies from the intended cut surface, alerts can be given to the surgeon and needed redirection movements of the surgical device displayed.

Finally, at the end of the operation, selected data can be automatically stored and/or inserted into a surgery report on the computer 110.

Figure 2:
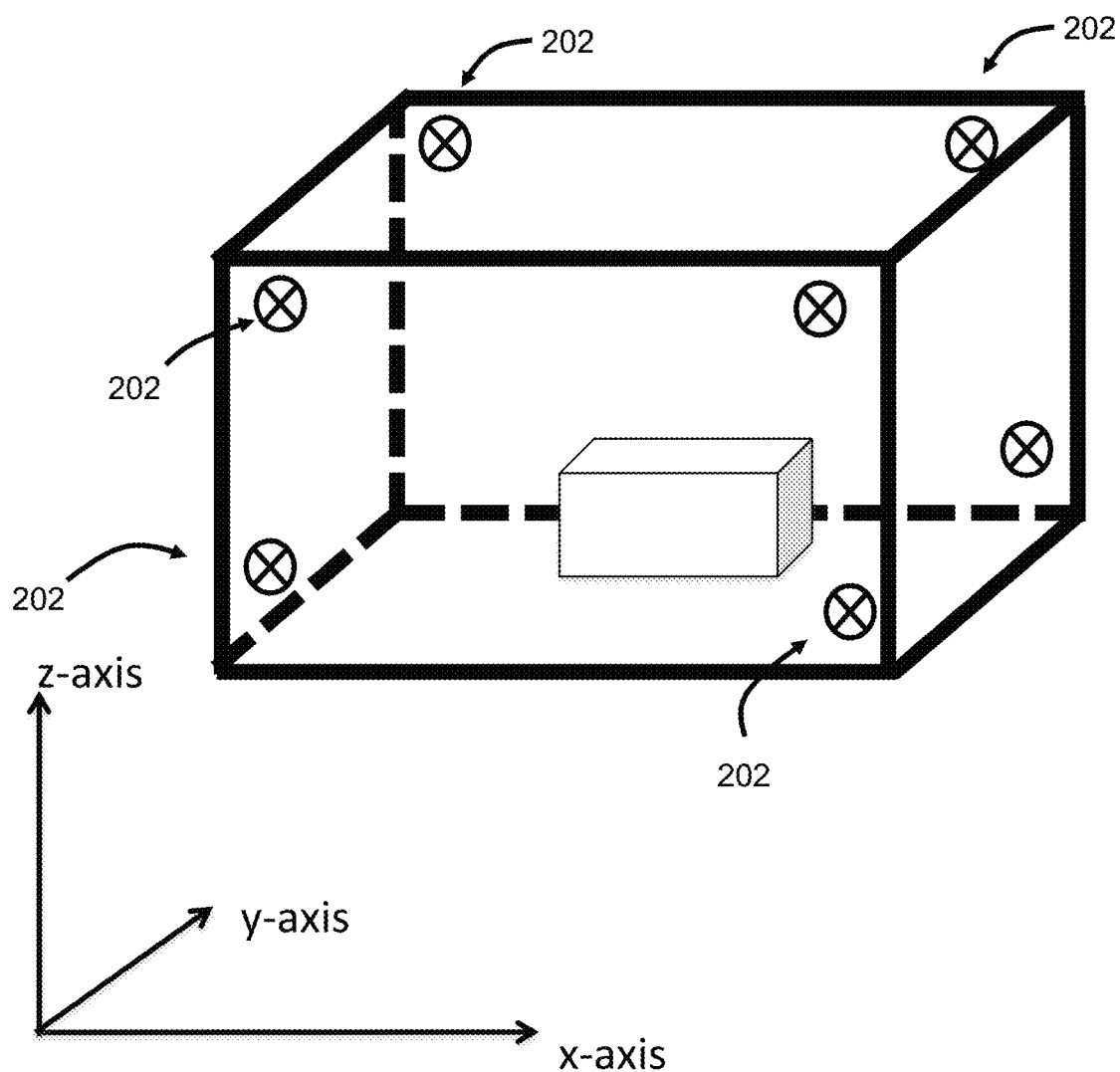
FIG. 2 depicts an example setup for an intelligent operating room which has an internal coordinate system.

FIG. 2 depicts an implementation of the intelligent operating room with an internal coordinate system. In the illustrated example, six or more transmitters (or receivers) 202 are placed at specific locations within the room where they will not interfere with the operation. Distances between all possible pairs of transmitters are measured with appropriate precision, e.g. and without limitation to the nearest millimeter. A coordinate system may be established that is unique to the operating room. For purposes of illustration, the X axis is in the long direction of a rectangular cuboid room; the Y axis is the shorter horizontal dimension, and the Z axis is the vertical (height) dimension. TDM (time division multiplexing) FDM (frequency division multiplexing) and other techniques may be used for the transmitted signals. For example, each transmitter (or receiver) 202 may emit (or receive) a signal according to a specified schedule. The signals 116 (FIG. 1) could be all of the same frequency in the EM spectrum but with different pulse characteristics, or of differing frequencies. One or more receiver (or transmitter) elements, e.g. reference point markers 106 (FIG. 1), receive (or transmit) the signals. Time of flight between transmitter/receiver pairs is used to calculate distances between transmitters and receivers. For example, and without limitation, the emitted signals may include a transmit time stamp that can be compared with a received time stamp to calculate signal flight time based on the time delta between the timestamps. The time difference can be used to calculate a corresponding unit of length distance from the transmitter based on the speed of the signal. Each calculated length distance may define a sphere, and intersections of spheres from multiple transmitters may be used to pinpoint the location of each receiver element. Thus, the patient and the surgical device can be spatially located within the operating room, and registered with respect to the 3D patient data set.

Figure 3:
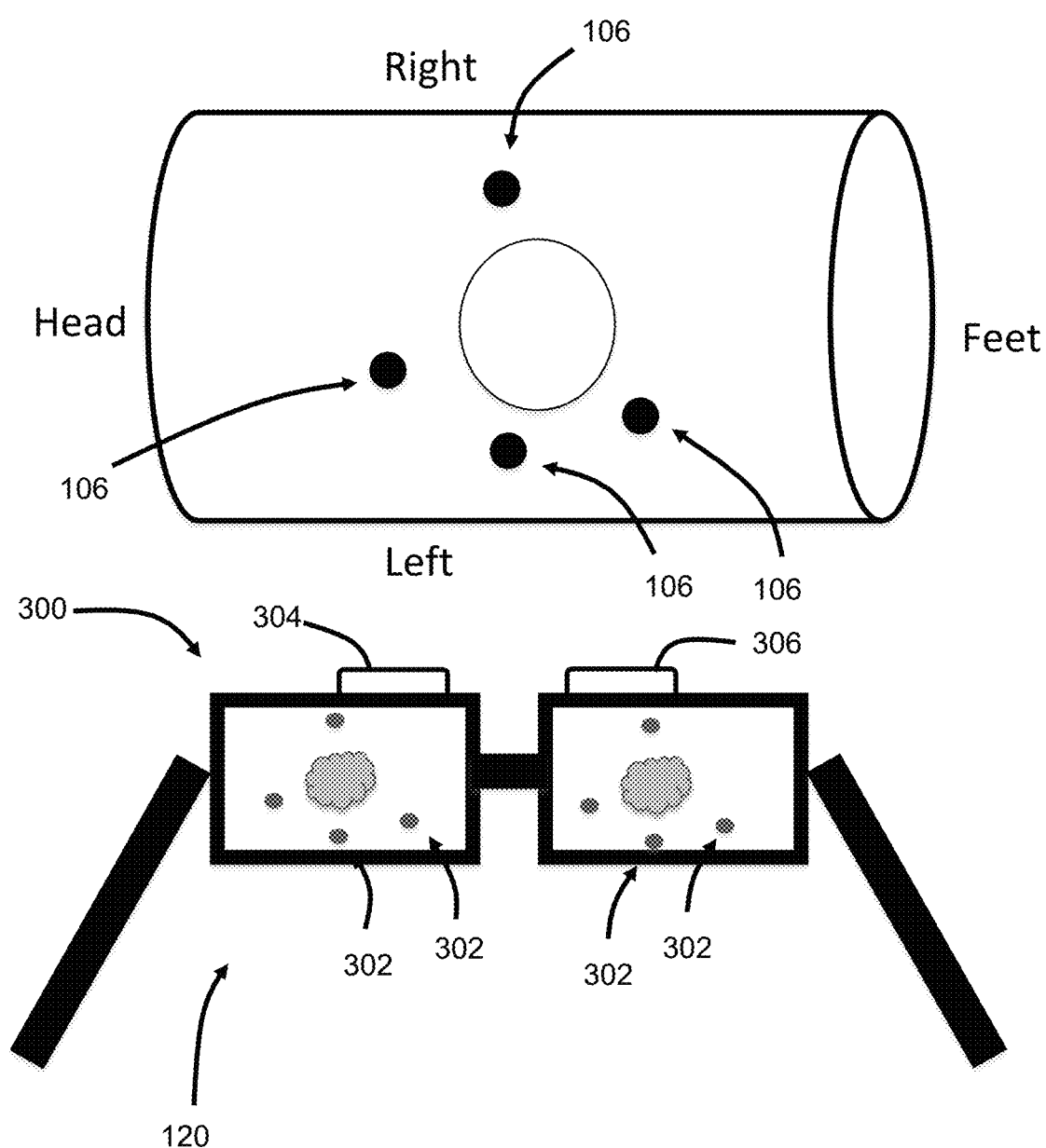
FIG. 3 illustrates placement of registration markers on a patient.

FIG. 3 depicts emplacement of the reference point markers 106. Note that the number of reference point markers depicted in the example is not limiting; any number of reference point markers that provide spatial location might be used. In order to attain the optimum registration of the reference point markers with the patient's 3D imaging dataset, the reference point markers should be positioned prior to the imaging examination. When the surgeon wears the augmented reality headset 120, the surgeon can see the actual reference point markers 106 in the real-world view and an image 300 that includes virtual reference point markers 302. The augmented reality headset 120 may be a free-standing object with a transceiver 304 for communication and inertial motion sensor system 306. It would display the images in a depth-3-dimensional fashion, such that true 3D imaging is performed with depth perception.

Figure 4:
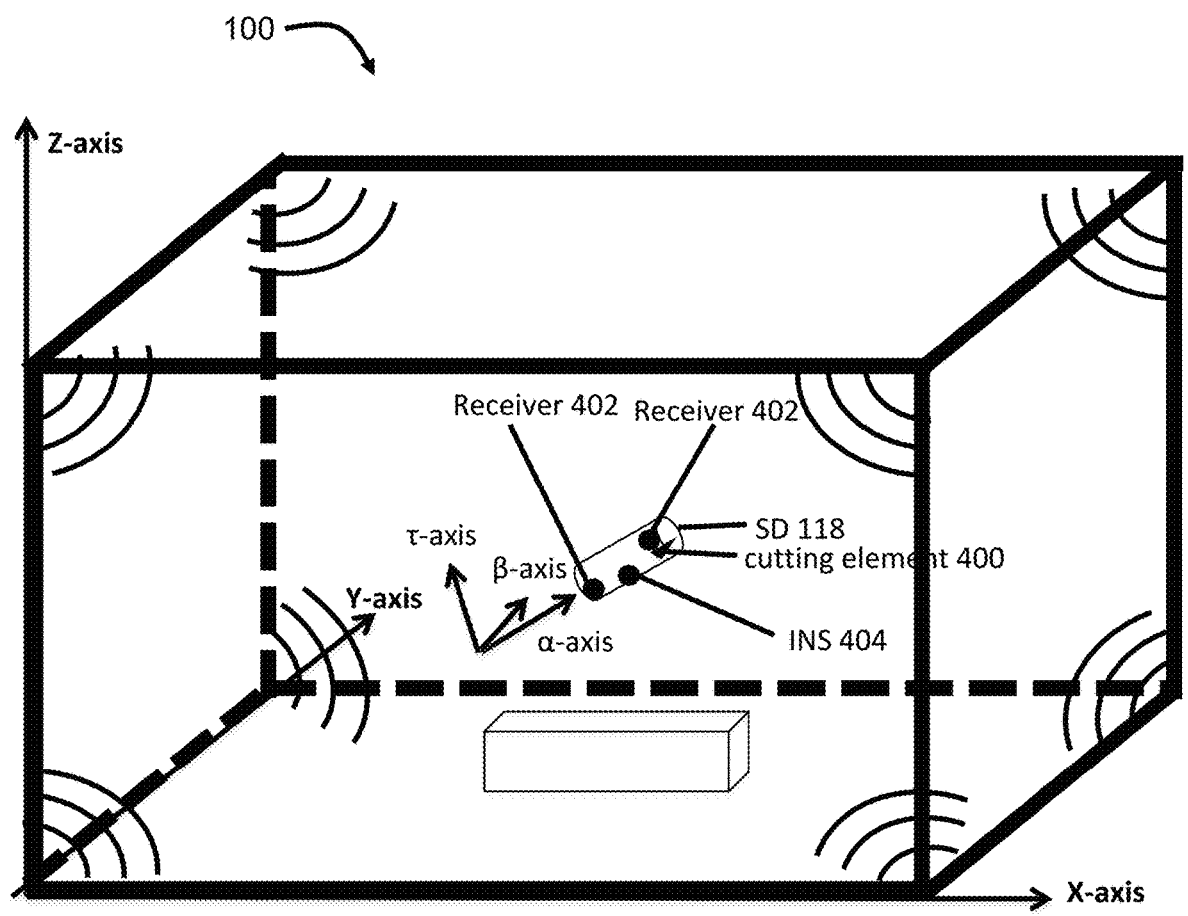
FIG. 4 illustrates determination of the location and orientation of the surgical device (SD) within the intelligent operating room coordinate system.

FIG. 4 depicts spatial location of the surgical device 118 within the coordinate system of the intelligent operating room 100. The system precisely calculates the spatial location (including orientation) of a cutting element 400 of the surgical device 118, and calculates and plots the trajectory of the cutting element at any point in time (actual trajectory before the current time and anticipated trajectory after the current time) both within the patient and within the patient 3D data set. Two or more receiver (or transmitter) elements 402 are positioned at non-cutting portions of the surgical device 118 to facilitate determination of spatial location of the surgical device. The location of each receiver element (X, Y, and Z coordinates) within the operating room is determined, and angles $\alpha$, $\beta$, and $\tau$ are computed relative to the X, Y, Z axes, respectively. Based on the calculated spatial location of the surgical device, and the known dimensions of the surgical device and cutting element, cutting edge coordinates are thereby known. Roll of the surgical device may be calculated using data from the inertial motion sensor 404 and the known geometry of the surgical device. The surgical device 118 continuously transmits data from its inertial motion sensor and (receivers if the operating room coordinate system is being used) via the communication system. The computer continuously tracks the surgical device and generates various display options. When a particular display is selected by the surgeon, the computer sends the display to the HDU via the communications system. Thus, an incision can be monitored and forecast in three dimensions with respect to the patient.

Figure 5:
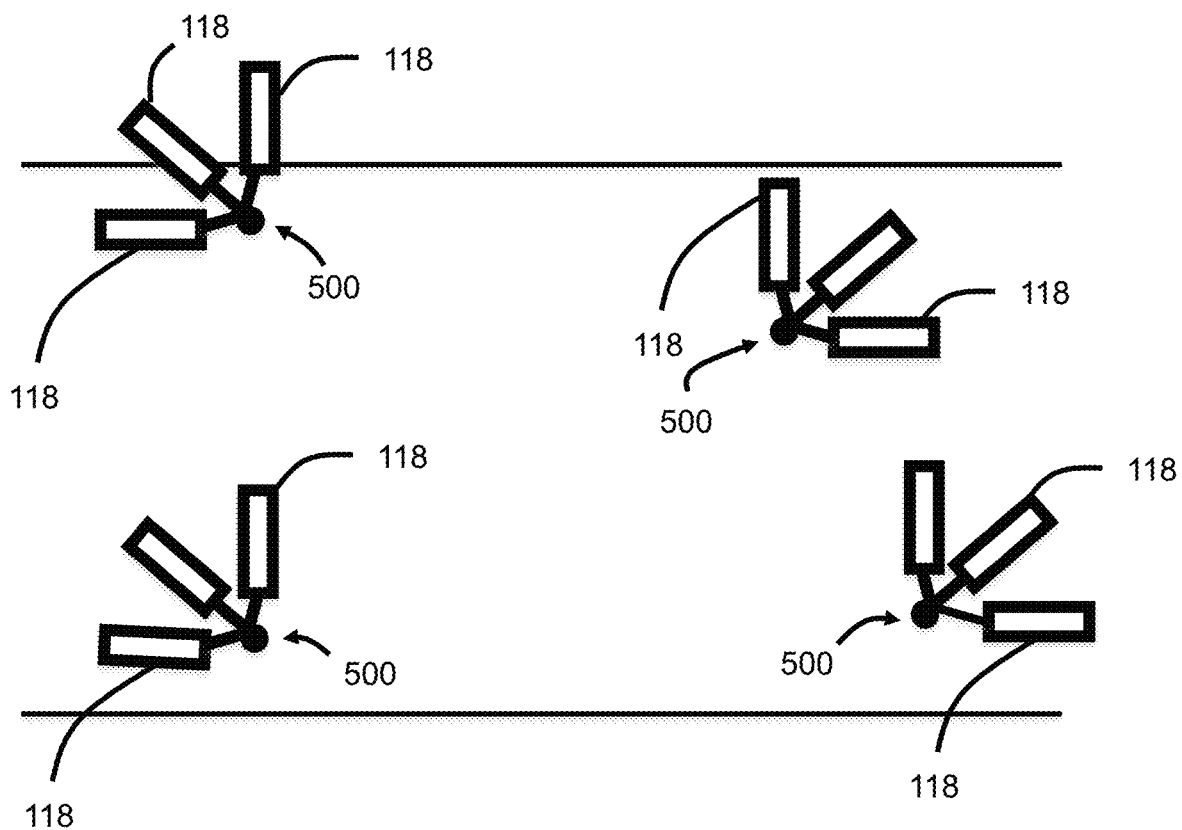
FIG. 5 illustrates a patient coordinate system.

FIG. 5 depicts a patient coordinate system. To register the surgical device 118 with respect to registration points 500, e.g. reference point markers 106 (FIG. 3), the surgical device is positioned in contact with each of the registration points from three approximately perpendicular angles representing the X, Y, and Z axis, respectively. By convention, the X axis could be parallel to the length of the patient; Y axis the horizontal width of the patient; and Z axis the depth or height above the operating gurney. Note that the region within the patient for the operation is within the overall volume encased by the registration points. Only four registration points are shown on this figure whereas a minimum of six points may be required for the registration process in practice.

Figure 6:
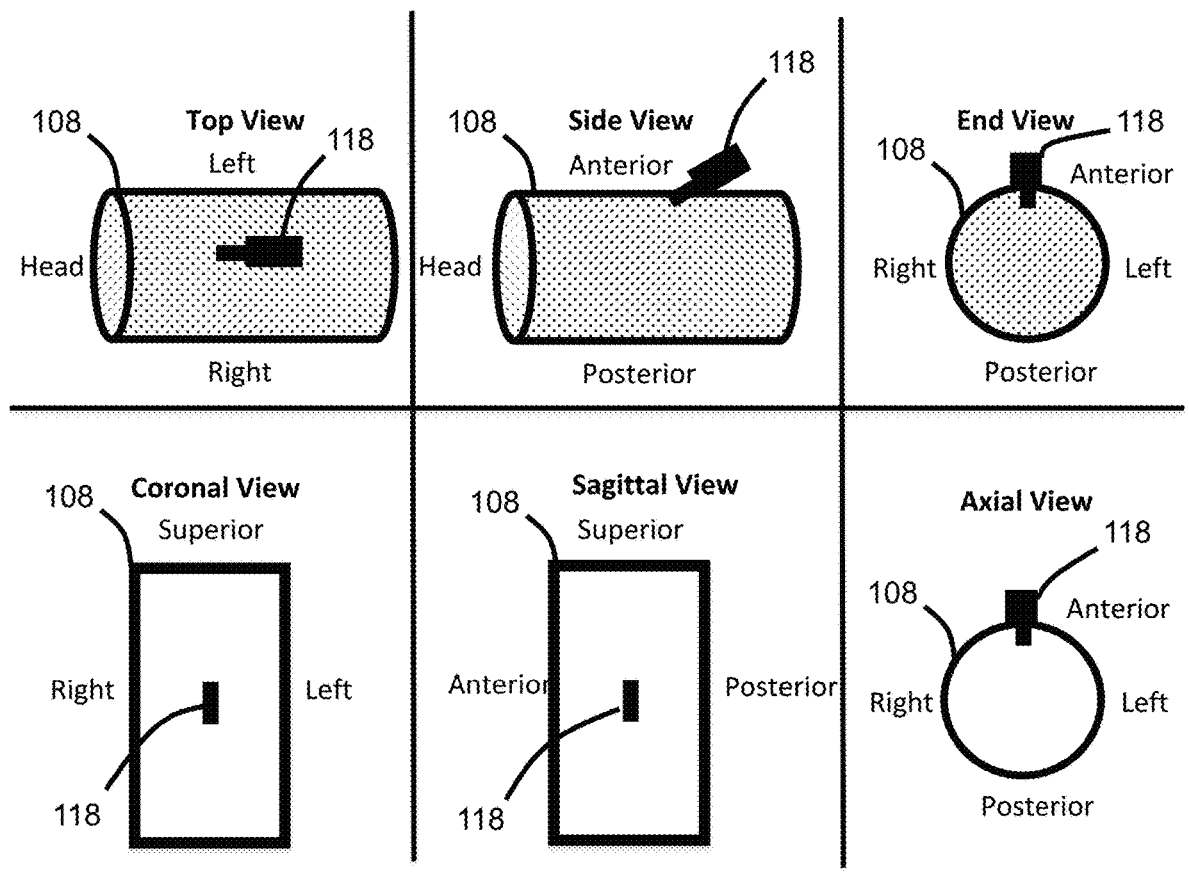
FIG. 6 illustrates axial, sagittal, and coronal views of the patient 3D data with the location and orientation of the SD within the 3D data set.

FIG. 6 illustrates spatial location of the surgical device 118 with reference to three views of the patient 108 (i.e., top, side, end) and three views of the 3D medical imaging data (i.e., axial, sagittal and coronal) with the location of the surgical within the 3D data set. Note that a 3D representation of a surgical device 118 is generated and superimposed onto the patient imaging dataset. These views could be displayed individually or collectively at any time at the direction of the surgeon. An option would be to show only a line showing the current location of the cutting edge of the surgical. Options to also display areas of concern and the shape containing tissue to be operated on could be displayed.

Figure 7:
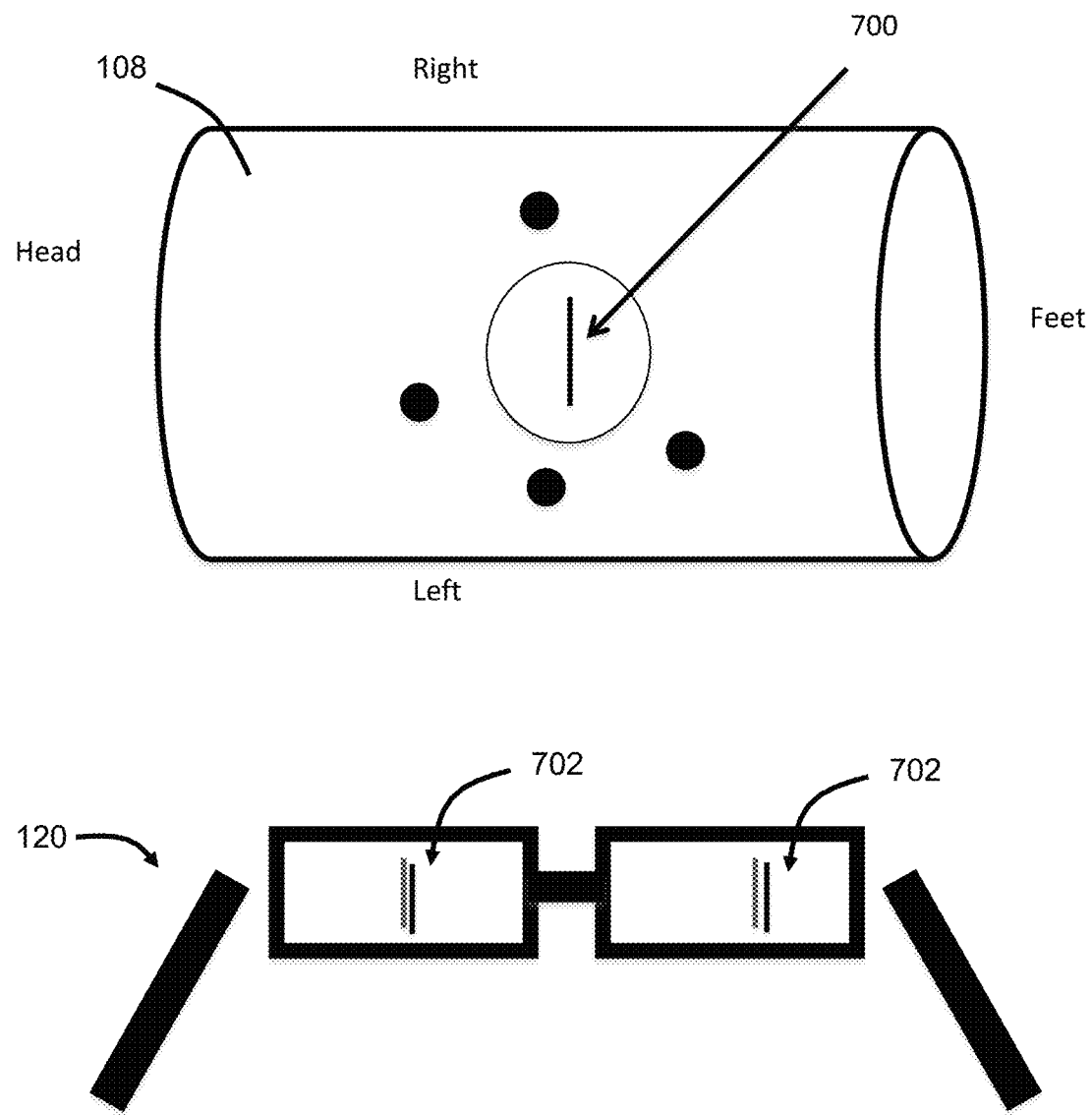
FIG. 7 illustrates the starting point, length, and depth of an incision as seen through the surgeon's augmented reality headset.

FIG. 7 depicts presentation of a planned surgical incision 700 on the HDU 120. A virtual incision 702 may indicate a starting point, length, and depth of a surgical incision that is a product of the pre-operative planning. The virtual incision may be presented on the surgeon's HDU 120 as a line (or other shape) superimposed on the patient 108 (i.e., from the stored pre-operative planning data within the patient 3D data set). Notes reflecting pre-operative planning may also be presented, e.g., proximity to regions of concern in red, whereas green indicates a planned cutting plane of the virtual incision.

Figure 8A:
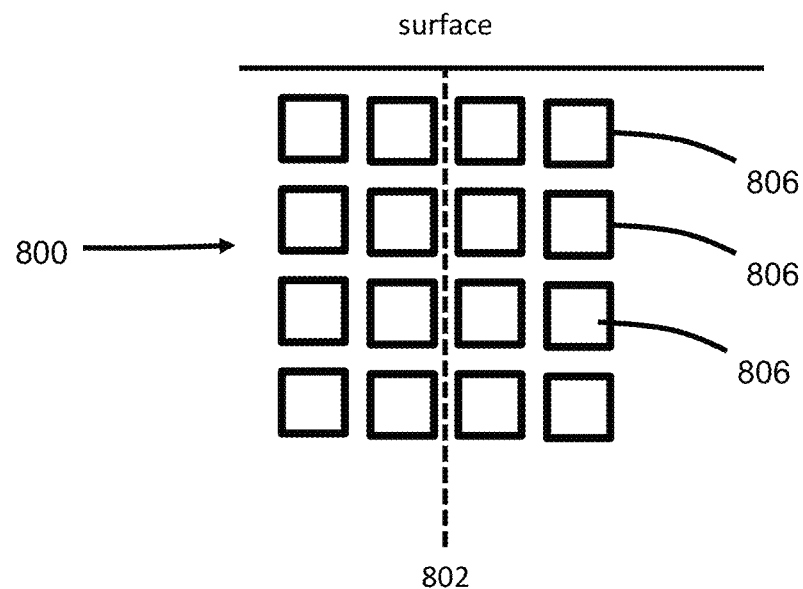
FIGS. 8A and 8B illustrate a surgical incision and tissue displacement along the cutting surface to reach the target.
Figure 8B:
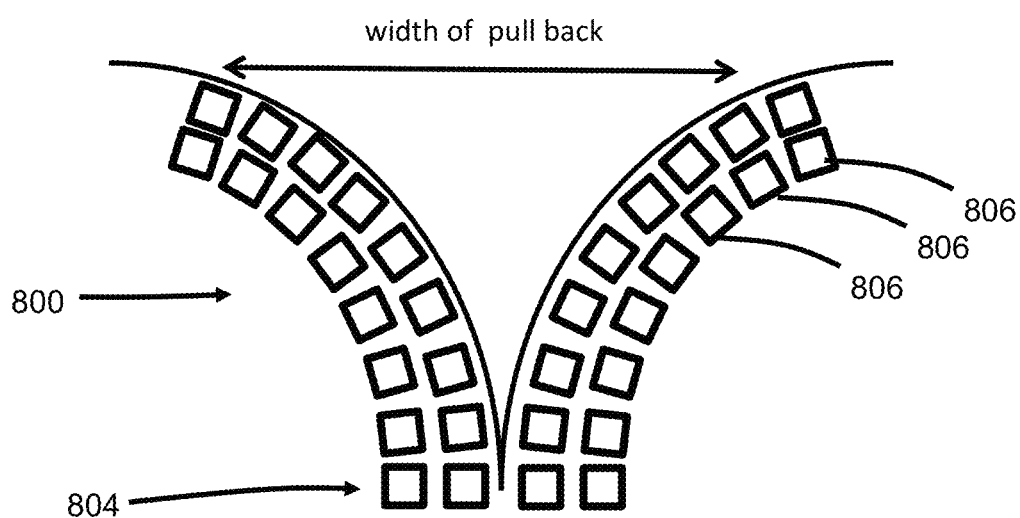

Referring to FIGS. 8A and 8B, during an operation, the surgeon cuts into the patient and displaces tissue 800 along the cut 802 to reach tissue 804 which is the objective of the operation. The displaced tissue 800 is not destroyed, but instead pulled to each side of the cut 802. As a result, the original 3D pre-operative medical imaging data set is no longer valid in the region of the cut. A representation of this displaced tissue is termed deformable tissue and it applies to the 3D data. The degree of deformation is based on the depth and length of the cut, the type of tissue adjacent to the cut, and the width the surgeon chooses to pull back the tissue. The deformation models (e.g., voxel displacement, re-sizing, re-orienting, adding new voxels, subtracting voxels, etc.) will be inputted into a real-time 3D medical imaging dataset for viewing, recording and analysis. Adjustment of the voxels 806 of this deformable tissue are illustrated in these figures. Voxels can be manipulated via compression, displacement and rotation.

Figure 9:
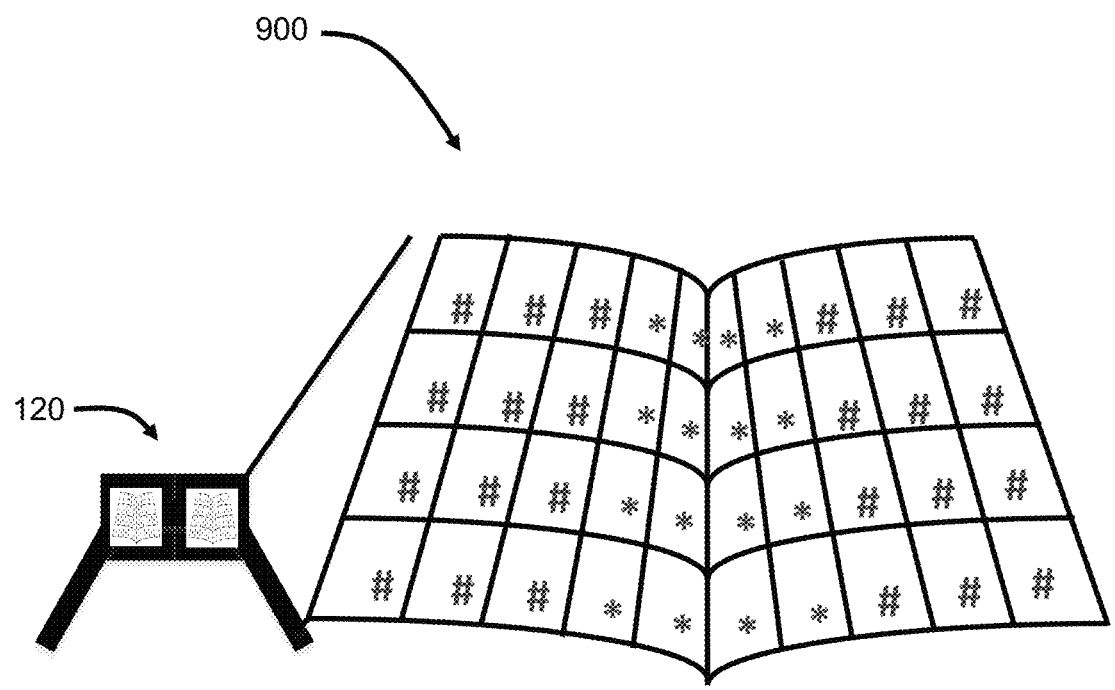
FIG. 9 illustrates the exposed deformable tissue from a top view as seen through the surgeon's augmented reality headset.

FIG. 9 illustrates exposed deformable tissue 900 from a top view as viewed through the HDU 120 at the surgeon's command. A metric grid may be superimposed on the image or patient to facilitate the surgeons understanding the cut depth at any time during the operation. Color coding may be used to indicate proximity to tissue which is the objective of the operation. For example: the tissue in the early stages at several centimeters from the objective tissue could be tinted light green. This would signify to the surgeon that the cutting could continue at the desired pace for this distance. The color could progressively change from light green to yellow as the cutting nears the objective tissue. Finally, changes to blue in close proximity to the objective tissue. Red areas would be designated as areas to avoid.

Figure 10:
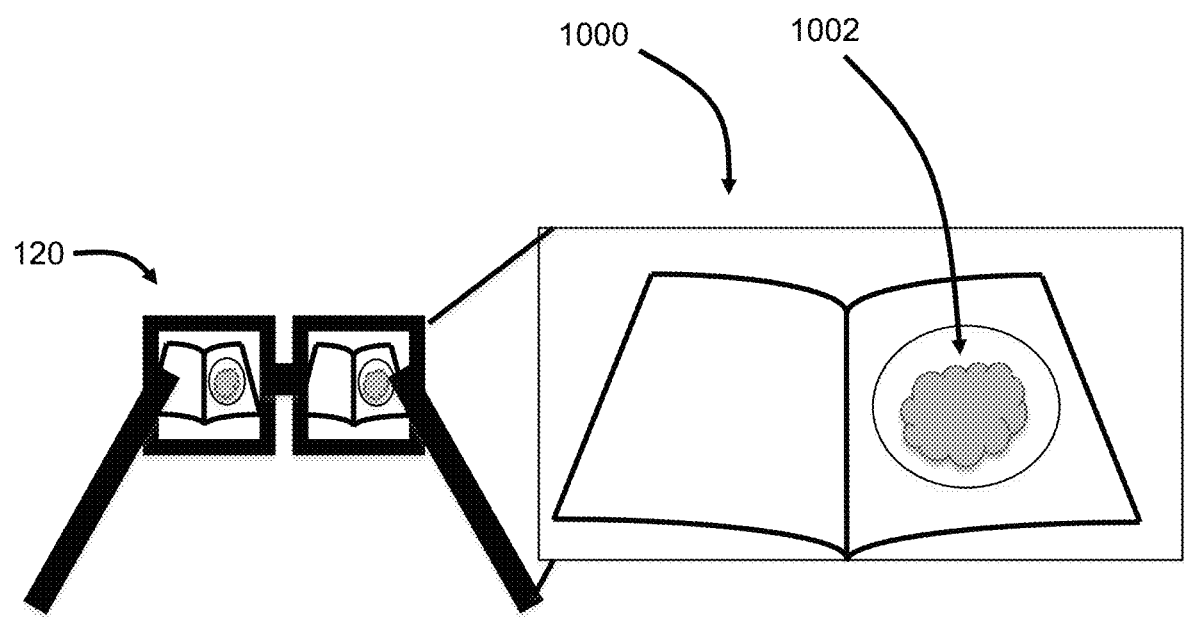
FIG. 10 illustrates a variable degree of transparency that can be selected so that the surgeon can peer through the deformable tissue and see other portions of the anatomy in the general region of the cut through the surgeon's augmented reality headset.

FIG. 10 illustrates exposed deformable tissue 1000 from a top view as viewed through the HDU 120. In the illustrated mode a variable degree of transparency is selected so that the surgeon can peer through the deformable tissue and see other portions of the anatomy (e.g., tumor 1002 in the deeper tissues) in the general region of the cut. The transparency may be selected at the surgeon's command. This would allow the mass to be visible through transparent tissue. As an example, if the cut were passing through fatty tissue and this fatty tissue pulled back (i.e., deformed), then this fatty tissue could be highly transparent and the surgeon could see the near the cut surface. This view would also be useful to show the surgeon where areas of concern delineated during the pre-operation planning. False color could be added to these areas of concern (e.g., red color for arteries in proximity to the cutting surface.)

FIG. 11 illustrates a side view of the patient 108 as viewed through the HDU 120, wherein the depth 1100 of the cut is shown as a line and the tissue 1002 which is the objective of the operation is highlighted. The anatomical site where the surgery is being performed 1102 is illustrated. Other portions of the body which could occlude viewing the line and the objective tissue are transparent. At this juncture, the surgeon could prompt calculation of the distance between the cut line and the objective tissue. At the surgeon's command this line, objective tissue and metric could be displayed on the surgeon's HDU 120. In a similar manner, a top view could be generated and metrics calculated to area of concern. This too would be available for display on the HDU.

Figure 12:
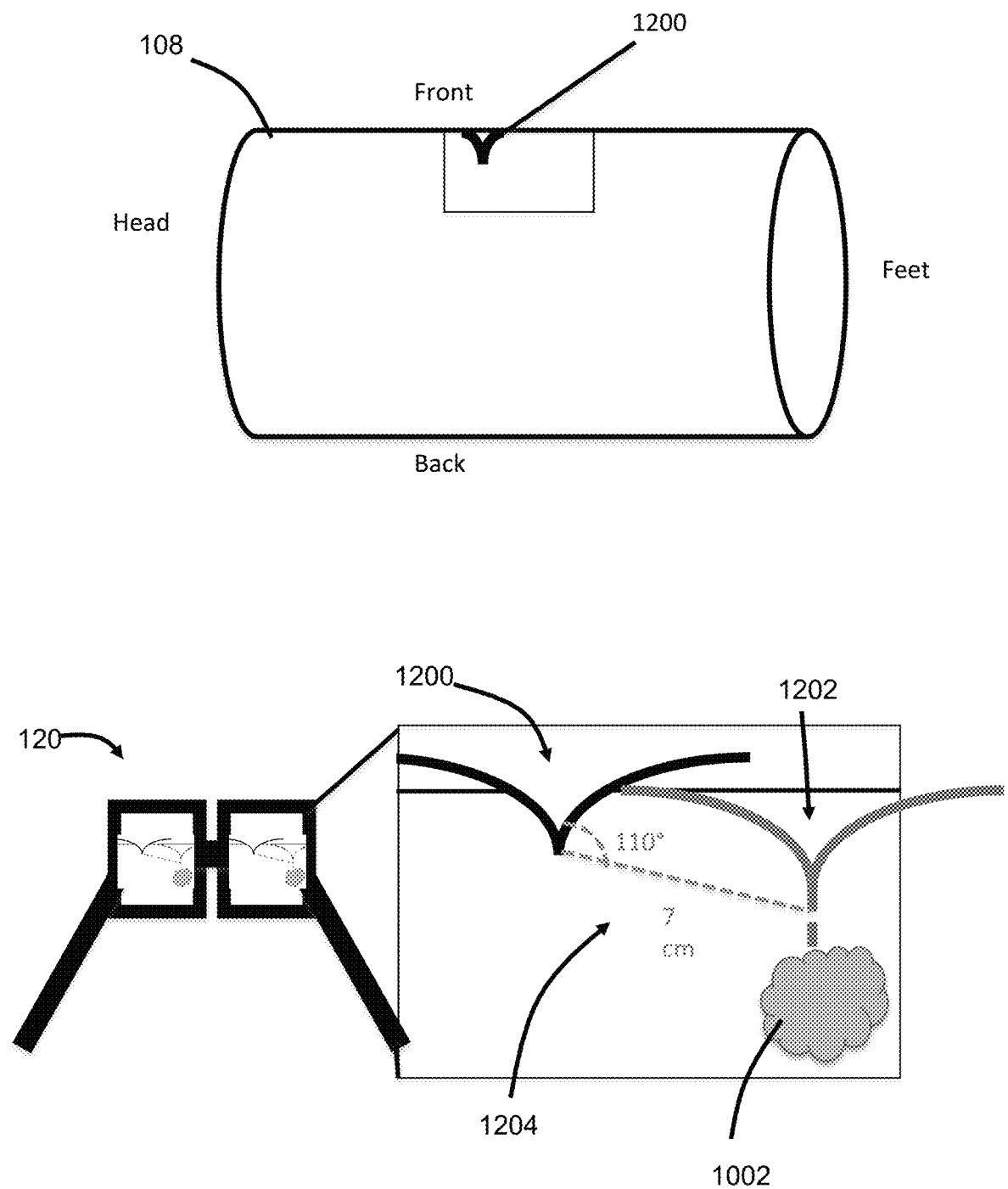
FIG. 12 illustrates the planned cutting surface vs. the actual cutting surface as seen through the surgeon's augmented reality headset.

FIG. 12 illustrates a condition wherein the actual incision 1200 has deviated from the planned incision 1202 as viewed through the HDU 120. This would be computed continually. Metrics that describe acceptable deviation limits may be specified, and if the actual deviation exceeds the specific limits then the surgeon would be alerted, e.g. via the HDU 120. At this juncture, the surgeon could choose to display on the HDU the two cutting surfaces (actual cutting surface and planned cutting surface). As a further assist to the surgeon, a corrective cut 1204 to reach the desired point on the objective tissue may be calculated and displayed on the HDU. Several options for display of the corrective cutting angle include a roll angle for the surgical device. This could be continuously calculated and displayed as the SD inertial motion sensor system noted changes in the roll angle and displayed further changes, as necessary.

Figure 13A:
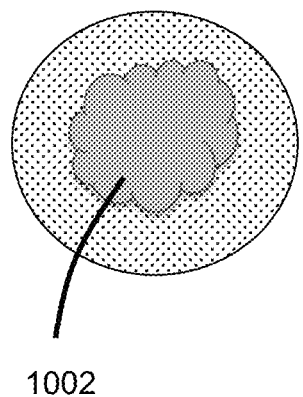
FIG. 13A through 13E illustrate encapsulation and review of tissue of concern/tissue which is the objective of the operation.
Figure 13B:
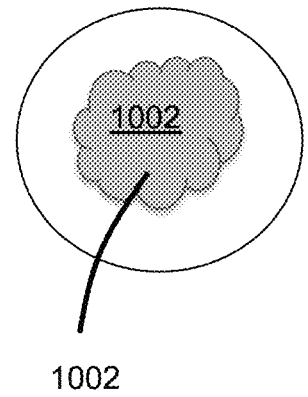

FIG. 13A illustrates encapsulation of the tissue of concern 1002 for the operation with a margin of benign tissue surrounding the tissue of concern within this encapsulation. The segmentation process is then applied as shown in FIG.

Figures 13C, 13D:
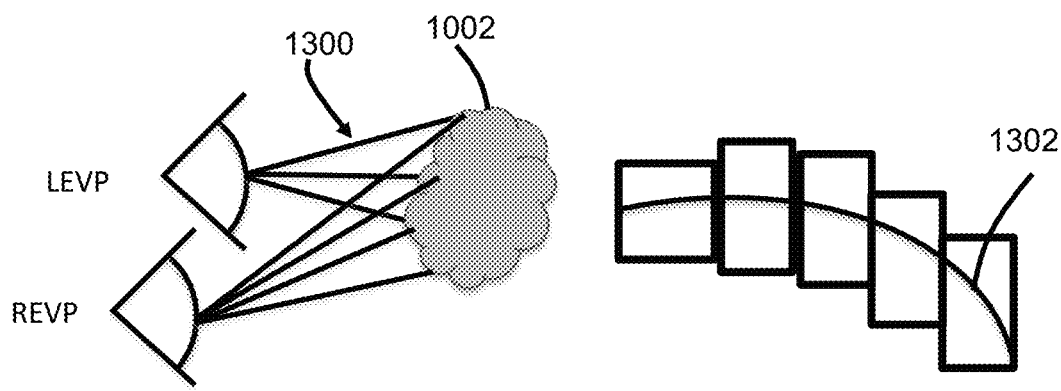
Figure 13E:
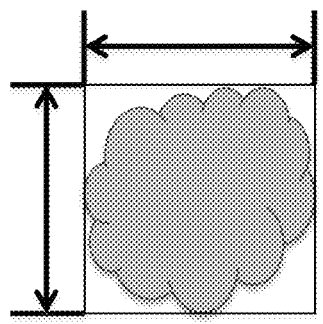

13B, and then tissue which is extraneous to the to the operation is then subtracted from the encapsulated volume as viewed through the HDU. Thus, only the tissue of concern remains in the encapsulated volume. At this juncture, a process is undertaken to ascertain which voxels are on the outer surface of the volume which contains the tissue of concern for the operation. This involves both the left eye view (LEVP) point and the right eye view point (REVP) as shown in FIG. 13C. For each of these viewpoints, rays 1300 are drawn which intersect with the volume and, for each ray, the minimum distance is recorded. This yields a surface which is convex and oriented toward the surgeon. If this process is conducted from multiple viewpoints, then a volume which represents the outer surface of the tissue of concern is established. At this juncture a smoothing algorithm 1302 may be applied wherein anomalies are largely eliminated through techniques such as Fourier transforms as shown in FIG. 13D. The resulting volume can then be displayed to the surgeon on the HMDs. Metrics would be available to show the dimensions of this volume as illustrated in FIG. 13E. The shape of the volume would be readily apparent, and this could guide the conduct of the surgical procedure.

Figure 14:
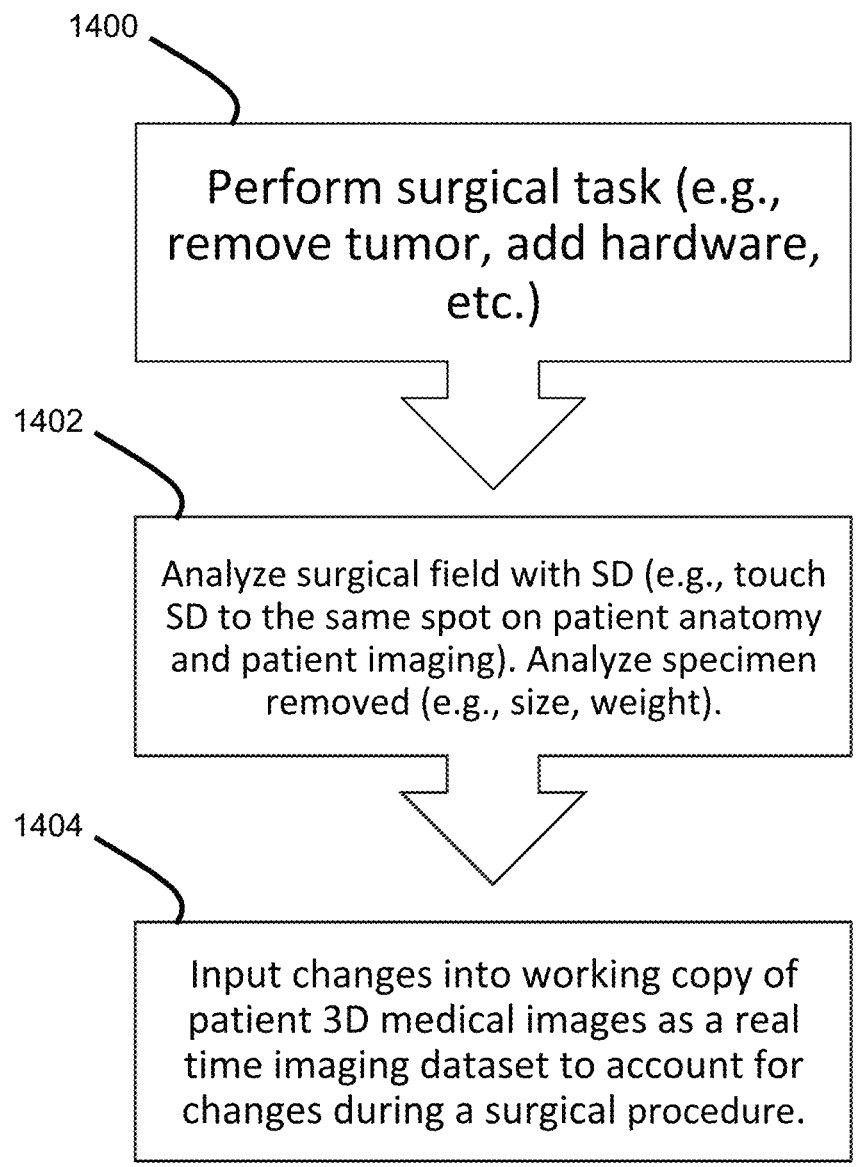
FIG. 14 illustrates a process for generating a real-time imaging dataset to better approximate the current surgical anatomy with reference to FIGS. 15A through 15D.

FIG. 14 illustrates a process for generating a real-time imaging dataset to better approximate the current surgical anatomy with reference to FIGS. 15A through 15D. Initially, a real-time imaging dataset will be generated as part of the pre-operative imaging examination as shown in FIG. 15A. The surgeon performs a surgical task as shown in block 1400, such as removing a portion of the skull and a portion of a tumor. Next, the surgeon and medical team will analyze the surgical bed with the SD and resected elements as shown in block 1402 to generate size, shapes, weights, tissue components of the removed elements as shown in FIGS. 15B and 15C. The shape of the surgical cavity will be determined. Next, the matched volumes are removed from the medical imaging dataset as shown in FIG. 15D. The resulting image will be a modified real time of the actual patient anatomy during the surgery as shown in block 1404. In other surgical procedures, hardware is added. In these such situations, a digital 3D representation of the surgical hardware is superimposed into the medical image. The voxels will be stretched accordingly.

Figure 16:
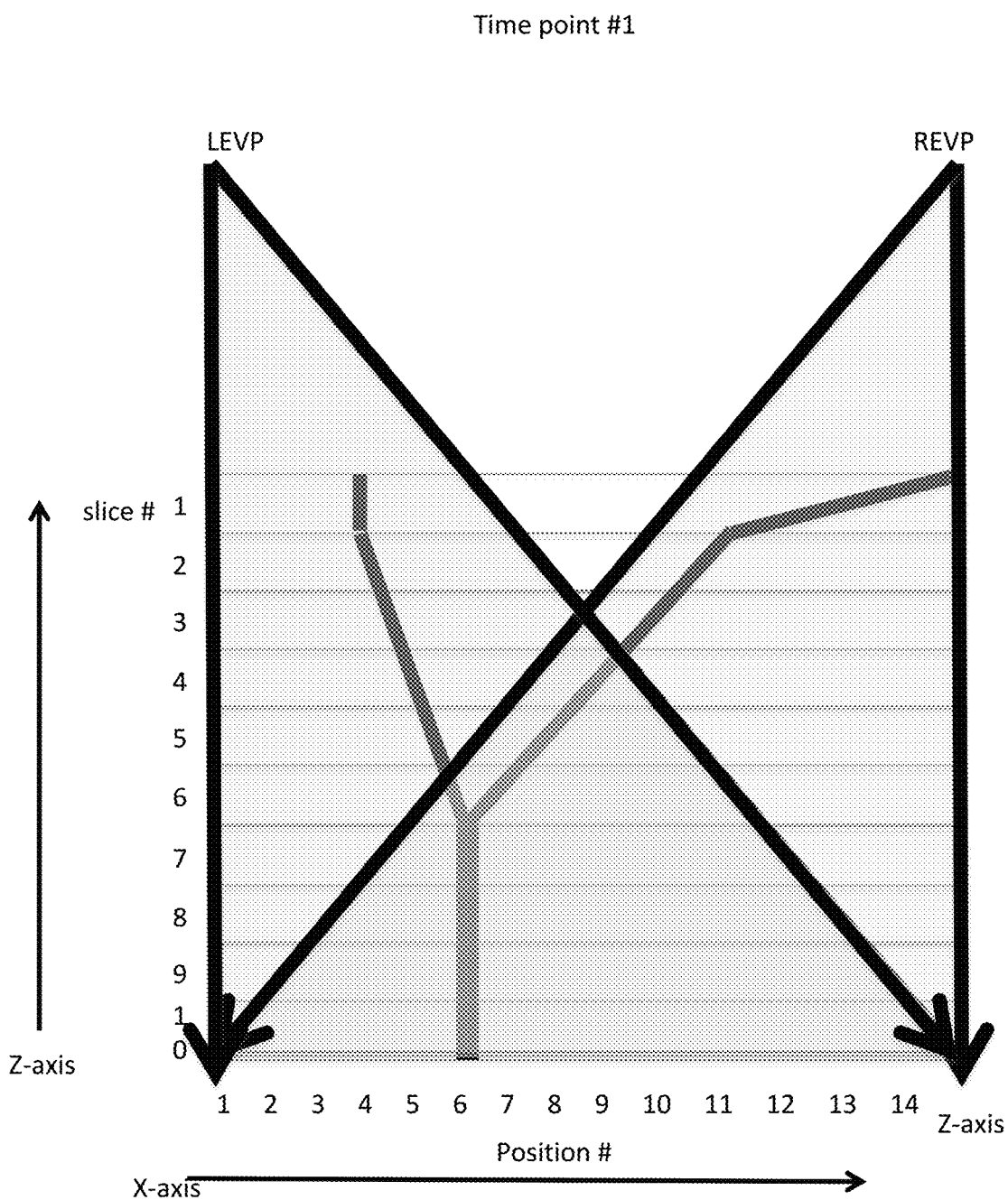
FIGS. 16, 17 and through 18 illustrate stacking of slices to generate a mobile volume.
Figure 17:
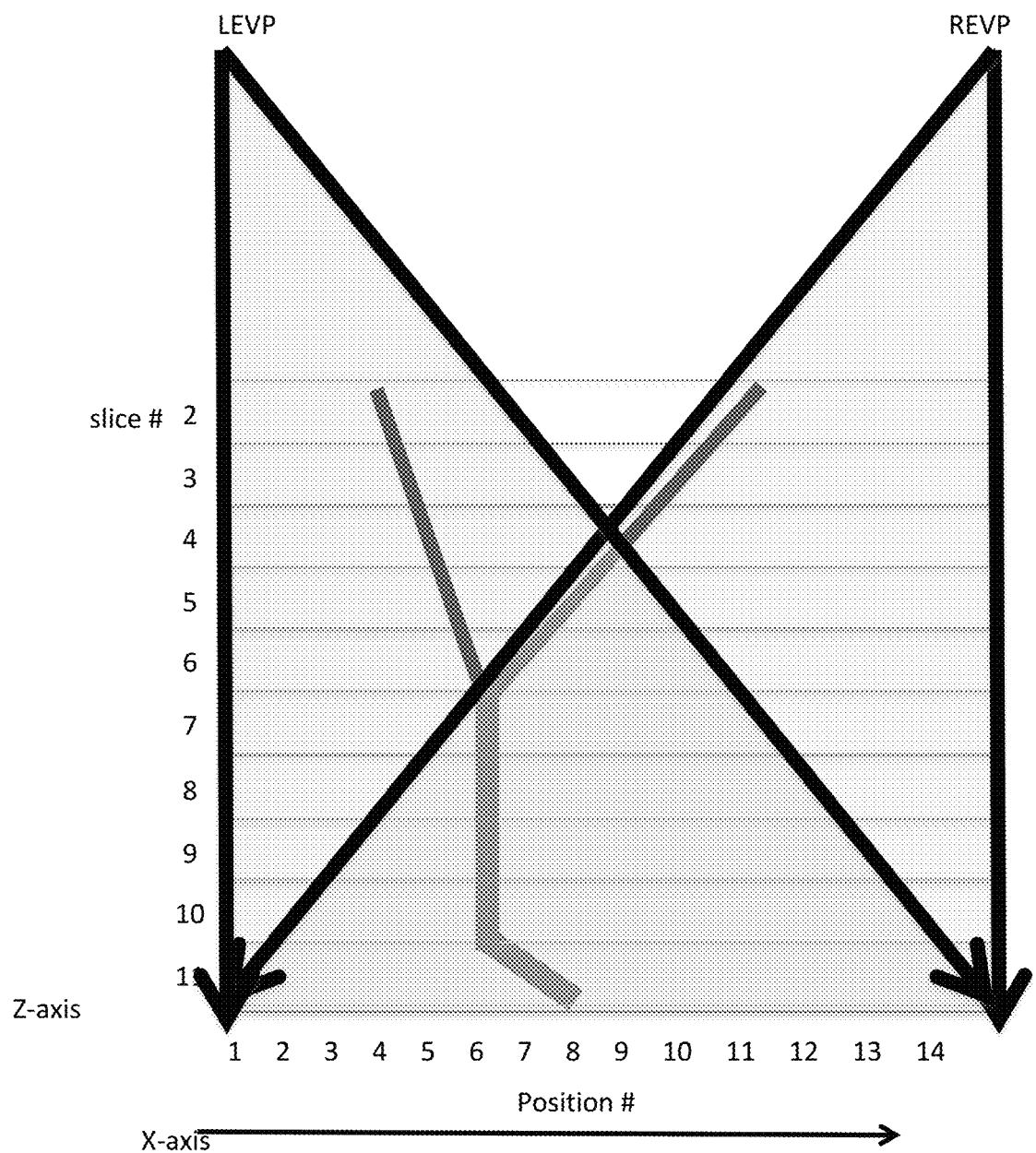
Figure 18:
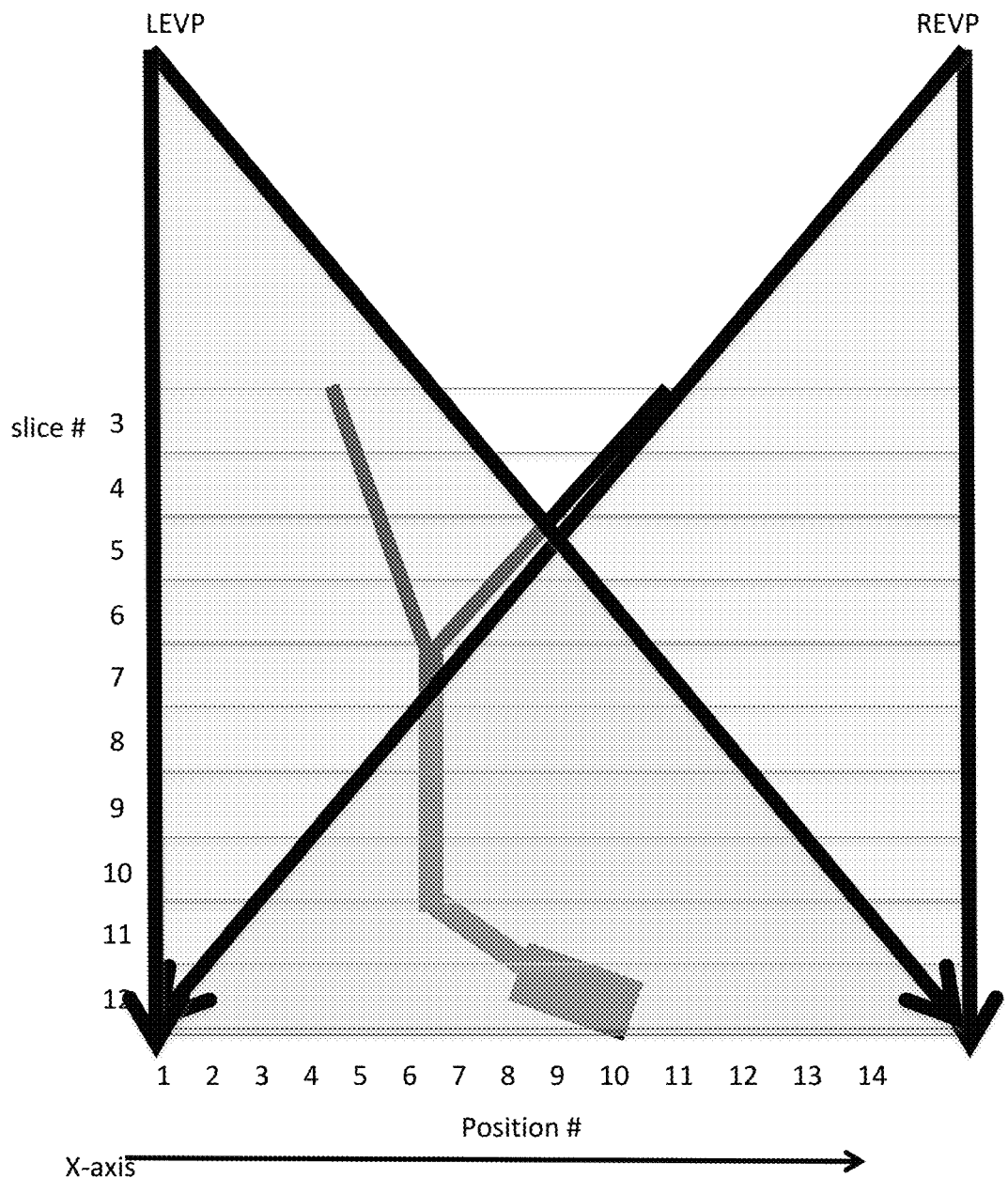

FIGS. 16, 17 and 18 illustrate stacking of slices to generate a mobile volume. In cases where the tissue anatomy is complex, the medical professional can have the ability to isolate the volume of patient tissues displayed down to a small number of slices (e.g., coronal slices) to form a stack. The initial head position displays slices 1-10. As the head position is moved toward the surgical field, the displayed images would include slices 2-11, then 3-12 and so on. This implementation of a mobile volume displayed allows the surgeon to view a complex structure, piece by piece. Although a progression of one slice per subsequent view was illustrated, the progression could be multiple slices with each progressive step. The degree of stepping would be controlled by the medical professional.

Figure 19:
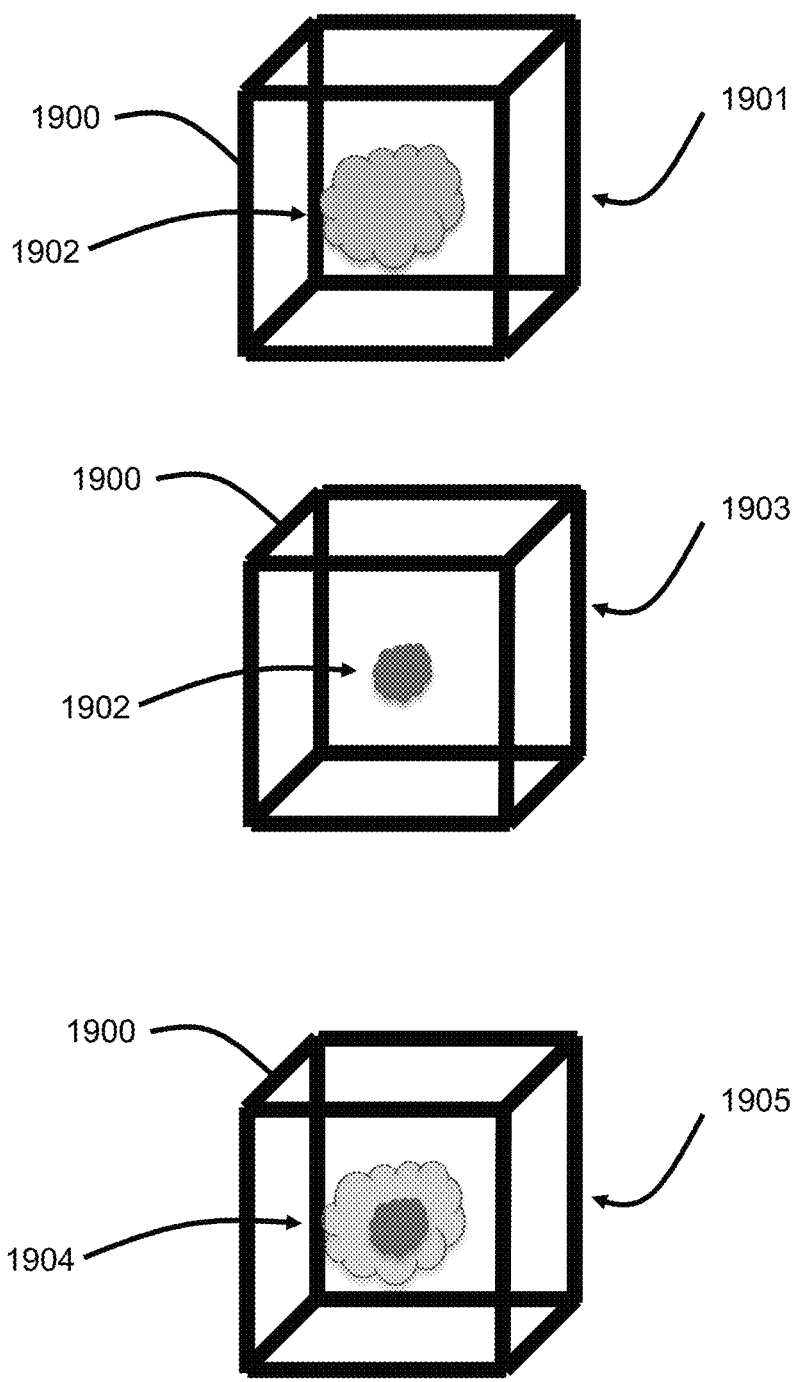
FIG. 19 illustrates a 4D cursor.

FIG. 19 illustrates a 4-dimensional (4D) cursor 1900 with dimensions including length, width, height and time. 1901 illustrates a first time point of the mass in the pre-treatment setting. Since a cancer mass 1902 can change in shape and size over time in its natural course (i.e., growth) or in response to neoadjuvant chemotherapy (NACT) (i.e., ideally shrink), a surgeon may be interested in the size and extent of the tumor at multiple time points. 1903 illustrates a second time point of the mass displayed at pre-operative scan, which is after neoadjuvant chemotherapy (NACT). Therefore, implementations will include displaying the mass in 3D at the time of diagnosis, after NACT, or superimposition 1904 of multiple time points in a single 3D image. 1905 illustrates superimposition of mass at time point #2 and time point #1 and provides surgeon with insight as to where the mass was previously located.

Figure 20:
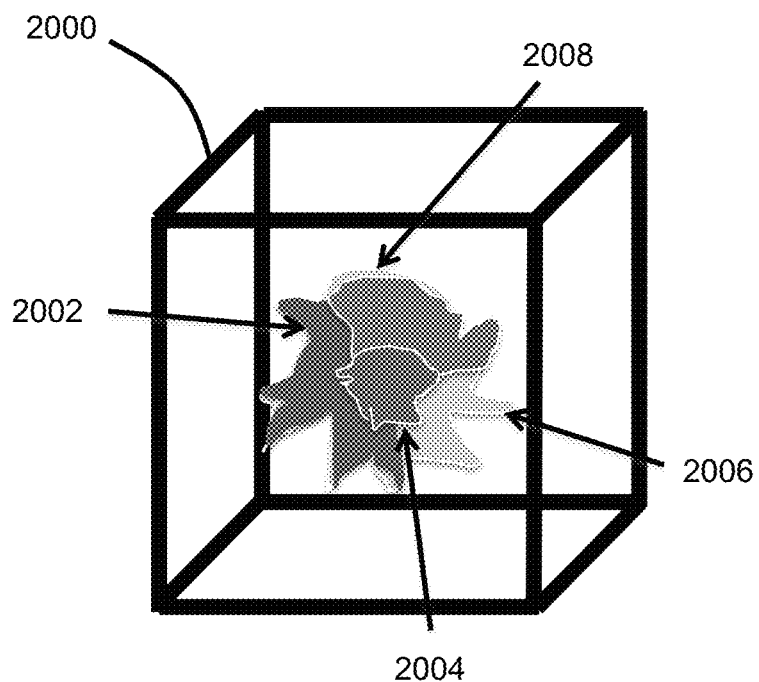
FIG. 20 illustrates a 5+ multidimensional cursor.

FIG. 20 illustrates a 5+ multidimensional cursor 2000. In addition to the standard volume dimensions (length, width, height), additional user-selected dimensions will be provided. Since MRI imaging provides multiple sequences (e.g., T1-weighted, T2-weighted, diffusion weighted imaging (DWI), dynamic contrast enhanced (DCE), properties of each of these images can be selected to be displayed in the surgeon's augmented reality headset. Specifically, the areas of enhancement with washout kinetics 2002, which are concerning for tumor are color coded red.

The surgeon may deem this to be the most dangerous portion of the tumor and may elect to take the widest margin at this location. 2004 illustrates dark gray scale voxels added in from T1-post contrast sequence at time point #2. The surgeon may elect to take a medium side margin around this portion of the tumor. 2006 illustrates a light gray scale voxels added in from T1-post contrast sequence at time point #1. The surgeon may elect to take a medium side margin around this portion of the tumor. 2008 illustrates blue voxels indicate restricted diffusion on diffusion weighted imaging (DWI) sequence at time point #1. The surgeon may elect to take a medium side margin around this portion of the tumor.

FIG. 21 illustrates a method to use a multi-dimensional cursor. Step 2100 is to perform a three-dimensional image wherein at least some of the voxels in the dataset have at least two data units (e.g., a MRI scan of the brain with a T1-weighted sequence and a T2-weighted sequence, a 4-phase CT scan of the liver, etc.). For example, the voxel at the exact center of the caudate head of the brain would have a particular data unit (intensity unit gray scale) on the T1-weighted MRI image and a different data unit (intensity unit gray scale) on the T2-weighted MRI image. Step 2101 is to display a three-dimensional image (e.g., stack of 2D slices, volume rendered image, MIP image, D3D image, etc.). Step 2102 is to place a volumetric 3D cursor into a three-dimensional image, such as is performed in U.S. patent application Ser. No. 15/878,463, Interactive 3D cursor for use in medical imaging. Step 2103 is to use properties of the 3D cursor (e.g., boundaries of the 3D cursor, which separate the inside of the cursor from the outside of the cursor) to divide the three-dimensional image into at least two sub-volumes (e.g., sub-volume of voxels inside of the volume-subtending 3D cursor and sub-volume of voxels outside of the volume-subtending 3D cursor). Step 2104 is to assign (e.g., via user input) at least one sub-volume a different dimension (e.g., a different phase, a different MRI sequence) from at least one other portion of the three-dimensional image. 2105 illustrates a T2-FLAIR image of the brain, which represents the same volume in a "first dimension". 2106 illustrates the volumetric 3D cursor. 2107 illustrates the T2-weighted image, which represents the same volume in a "second dimension". The contents of the 3D cursor could then switch to a T1-weighted image, which would represent the same volume in a "third dimension". Then, to a GRE image, which would represents the same volume in a "fourth dimension". Switching the volume could be via scrolling or keyboard or voice or joystick or other inputs. The 3D cursor could be moved, rotated, re-sized or other options discussed elsewhere in this patent.

Figure 22:
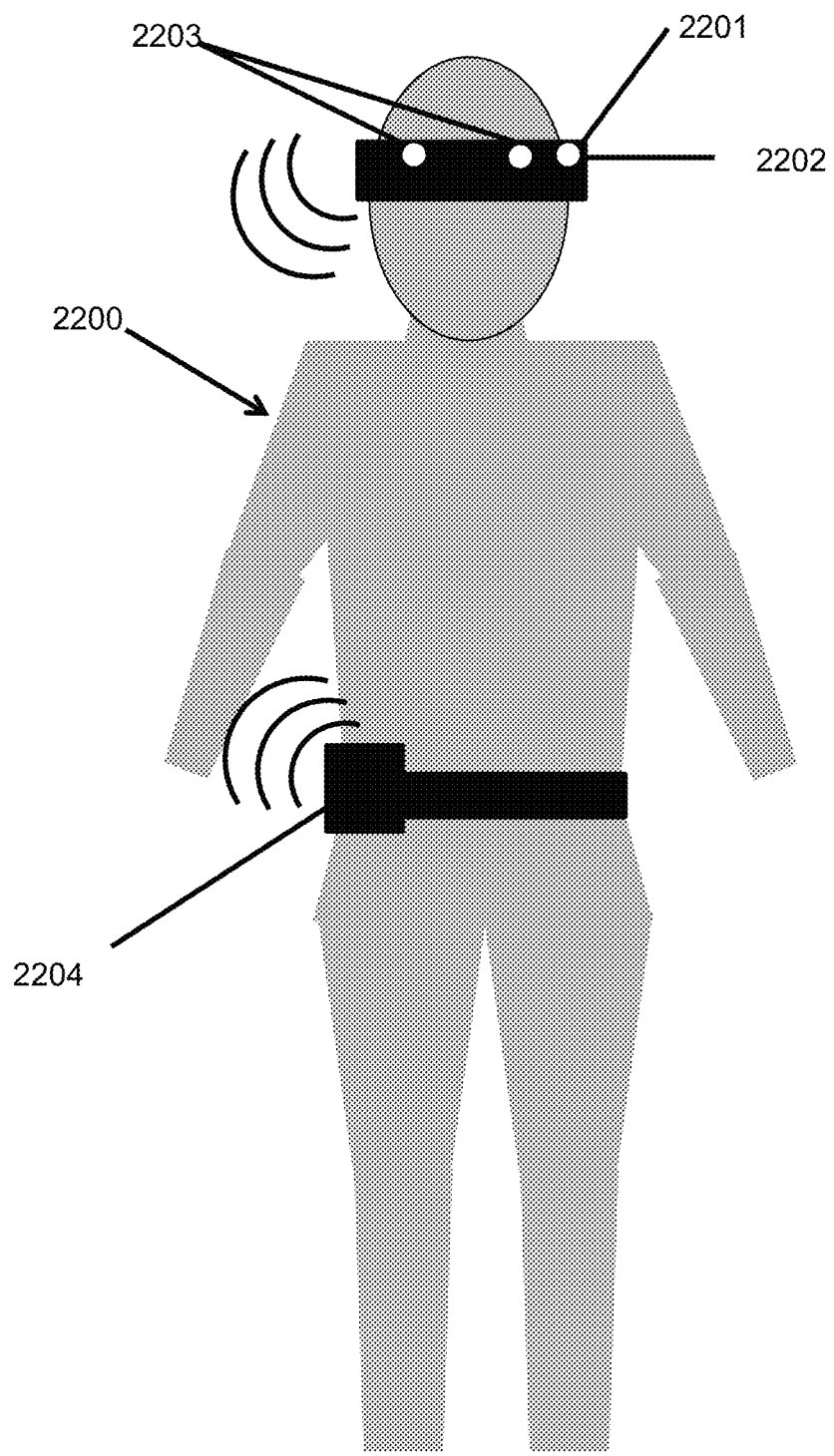
FIG. 22 illustrates a person wearing Smart Glasses System (SGS).

FIG. 22 illustrates a person wearing Smart Glasses System (SGS). This illustration depicts a person 2200 wearing the SGS 2201. Key elements of the SGS include: the Laser Range Finder (LRF) 2202; a TV camera; and Low Light Level TV or FLIR cameras 2203 which are mounted on the eye glasses frame. Not visible in this view of the system are: transmit and receive auditory system; orientation sensors (inclinometers/Inertial Measurement Unit (IMU); wireless element which communicates with the computer element and battery. The computer element 2204 is shown attached to the waist. The computer being stored on the operator's waist is preferable to take the weight off of the head. Additional options include an eye tracking system. The gaze direction of the user can be used to guide the direction of the Laser Range Finder (LRF) 2202; and Low Light Level TV or FLIR cameras 2203. For example, if the user is continuously looking to the left at 30 degrees leftward horizontal angle and 10 degrees downward vertical angle, then the Laser Range Finder (LRF) 2202; and Low Light Level TV or FLIR cameras 2203 can preferentially gather data in the same field of view of the user's gaze.

Figure 23:
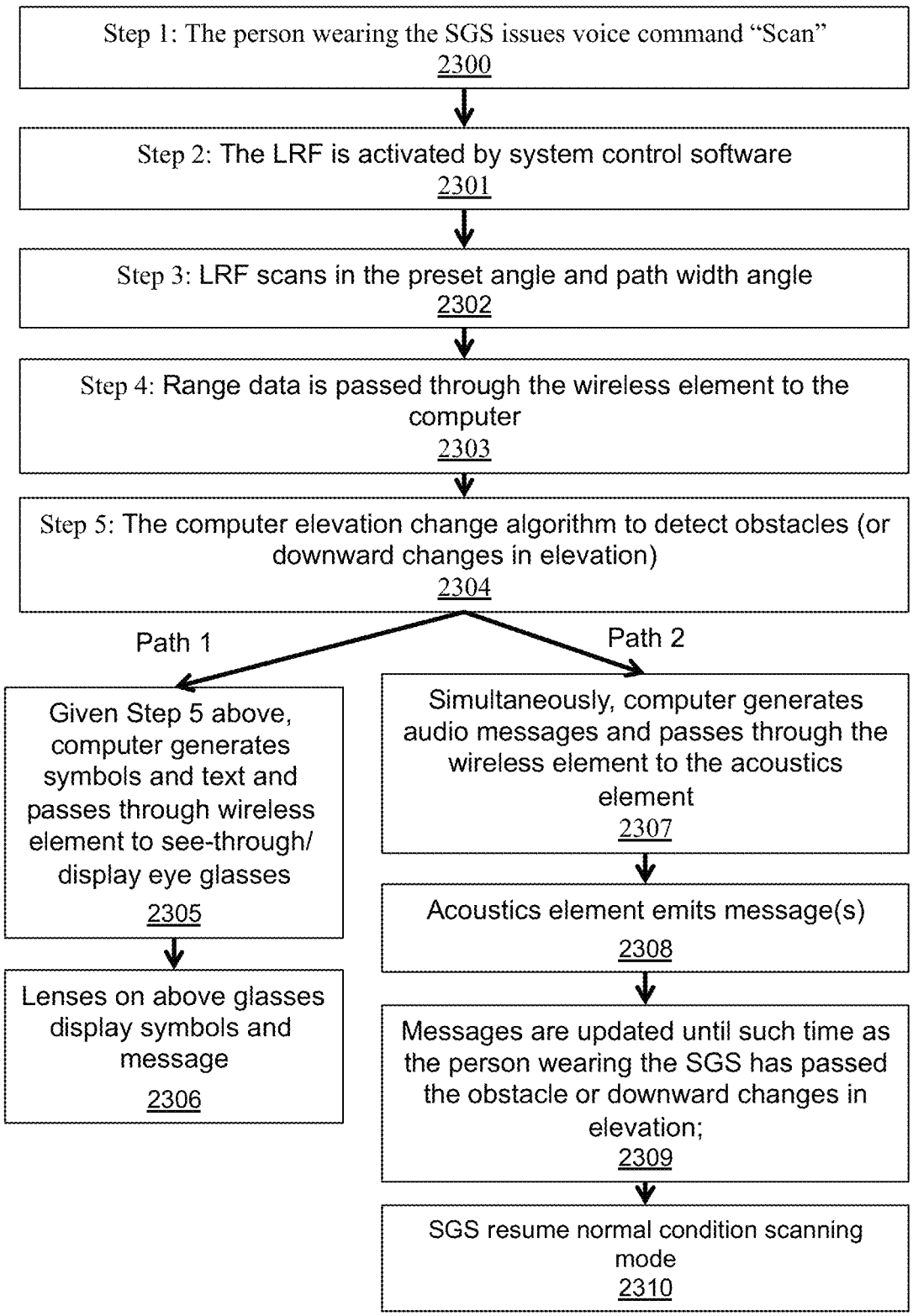
FIG. 23 is a flow chart of the system in LRF scanning mode.

FIG. 23 is a flow chart of the system in LRF scanning mode, assuming the system has been calibrated. The LRF scans in front of the person and passes range data to the computer which is running an algorithm to detect changes in the surgical cavity or operating room. Alternatively, it can detect changes in elevation—indicative of stairs, curbs, irregularities in sidewalks, obstacles, etc. Given nonuniformity in the path ahead, the computer generates a symbol to be passed to the display portion of the SGS lenses. The symbol (e.g., a colored line in the case of stairs) is located on the display corresponding to the location of the edge of the stairs as viewed by the person wearing the SGS. Distance may be displayed in a text box and an audio warning sounded. An example algorithm is as follows. Step 1 2300 is for the person wearing the SGS to issue the voice command "Scan". Step 2 2301 is the LRF is activated by system control software. Step 3 2302 is LRF scans in the preset angle and path width angle. Step 4 2303 is where the range data is passed through the wireless element to the computer. Step 5 2304 is where the computer elevation change algorithm (e.g., to detect obstacles, to detect downward changes in elevation). At this juncture, two paths can occur. In the first path, step 2305 states that given Step 5 above, computer generates symbols and text and passes through wireless element to see-through/display eye glasses. Step 2306 is for the lenses on above glasses display symbols and message. In the second path, step 2307 is to simultaneously, computer generates audio messages and passes through the wireless element to the acoustics element. Step 2308 is to have the acoustics element emits message(s). Step 2309 is wherein messages are updated until such time as the person wearing the SGS has passed the obstacle or downward changes in elevation. Step 2310 is wherein SGS resume normal condition scanning mode.

FIG. 24 is a flow chart of the system in L3TV camera mode, assuming the system has been calibrated. Another mode of the SGS functioning to improve in visibility in low light level or dark conditions is as follows. During twilight and evening hours, one could turn on the Low Light Level TV (L3TV) or FLIR cameras and have the output projected onto the SGS lenses. This would retain stereoscopic vision in black and white. The LRF, could be running simultaneously. Step 1 2400 is for the person wearing the SGS issues voice command "TV". Step 2 2401 is for the L3TV cameras are activated by system control software. Step 3 2402 is wherein imagery generated by the cameras is passed through the wireless element to the computer which reformats it, if required. Step 4 2403 is wherein the computer passes imagery data through wireless element to respective lenses for display. Step 5 2404 is if voice command issues "zoom", then acoustics element passes signal through the wireless element to the computer. Step 6 2405 is wherein the computer recognizes the voice command and generates instructions to L3TV cameras to change fields-of-view (FOVs). Step 7 2406 is wherein instructions passed thru wireless element to L3TV cameras. Step 8 is wherein data generated by L3TV cameras goes thru above display process. Step 9 2408 is when zoom is no longer needed the person wearing the SGS issues voice command "Normal" and SGS resume normal L3TV cameras imaging mode.

FIG. 25 is a flow chart of the SGS situational awareness mode. In step 1 2500, the person wearing the SGS issues voice command "SA mode". In step 2 2501, the LRF is activated by system control software and operates as described in 1, above. In step 3 2502, the L3TV cameras are activated by system control software and operates in 2, above. In step 4 2503, acoustic signals received by the acoustic element are passed thru the wireless element to the computer. In step 5 2504, the computer analyzes acoustic data and applies detection algorithms for approaching/receding/stationary vehicles; generates messages accordingly; passes thru wireless element to display portion of lenses and acoustic transmit element. In step 6 2505, given there is an approaching vehicle and the person wearing the SGS turns head, if needed, for the vehicle to be in FOV the person could place crosshair on vehicle and issue voice command "Range". In step 7 2506, LRF provided range at specified intervals passes to computer via wireless element. Computer determines range rate changes and calculates time of arrival generates messages accordingly; passes thru wireless element to display portion of lenses and acoustic transmit element. In step 8 2507, given the person wearing the SGS is at a crosswalk, they may invoke zoom command per 2, above.

FIG. 26 is a flow chart of the SGS in initialize/calibrate mode. In step 1 2600, the person wearing the SGS issues voice command "Calibrate". In step 2 2601, the LRF is activated by system control software and operates as described in 1 2600, above; laser pointer with colored dot is activated. In step 3 2602, the person wearing the SGS point system crosshair to some recognizable point (e.g., corner of door frame) and checks where the laser pointer dot is with respect the crosshair. In step 4 2603, the LRF is adjusted, as needed to cause laser dot to coincide with center of crosshair.

Figure 27:
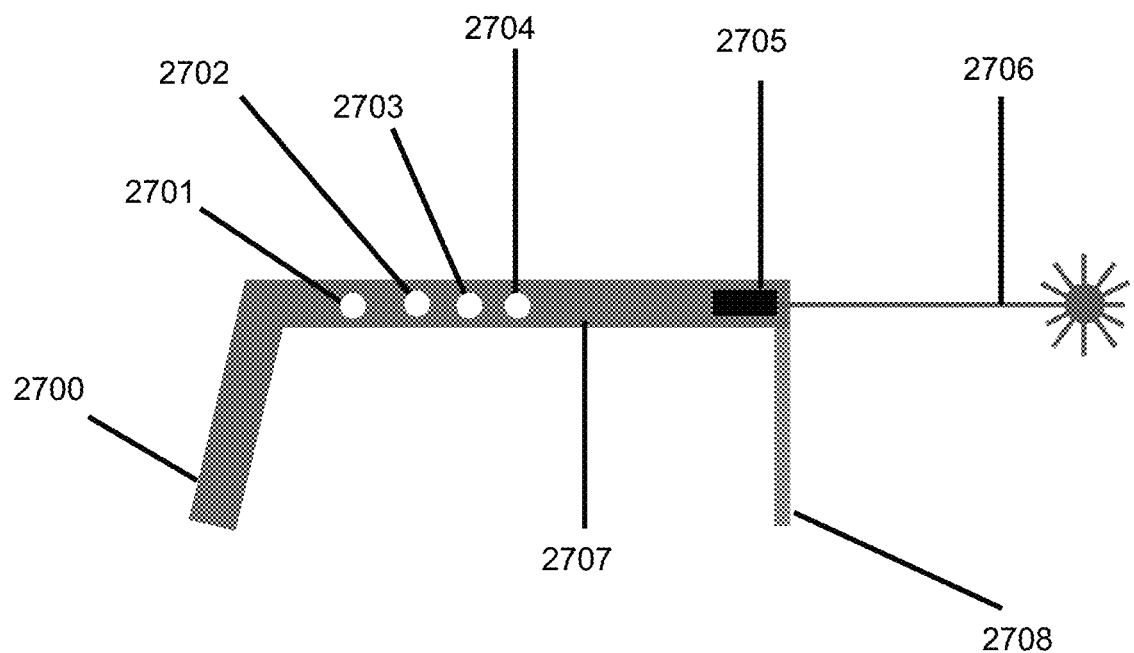
FIG. 27 is a side view of SGS illustrating key components.

FIG. 27 is a side view of the SGS illustrating key components. 2700 illustrates the back of the SGS, which hugs to the ears. 2701 illustrates the audio receive/transmit component. 2702 illustrates the transmit/receive function (e.g., Bluetooth). 2703 illustrates a computer. 2704 illustrates an inclinometer. 2705 illustrates a laser range finder. 2706 illustrates the laser beam with adjustable vertical and horizontal angle. 2707 illustrates the body of the SGS, which hugs to the side of the head. 2708 illustrates lenses. The preferred embodiment for the lenses is a transparent see-through lenses with embedded color digital display (for symbols and letters). The preferred embodiment for the laser range finder is to have a coincident colored dot transmitter. Additionally, an orientation sensor, such as an inclinometer/inertial measurement system can also be used. Such a sensor would be useful in detecting look angles of the individual. In addition, if an abrupt (or aberrant) change in look angle was in accordance with the user's head falling forward, then Additionally, an optional global positioning system can be implemented, which would be useful in the event that the individual is navigating. wireless digital transmission and receive communication system.

Figure 28A:
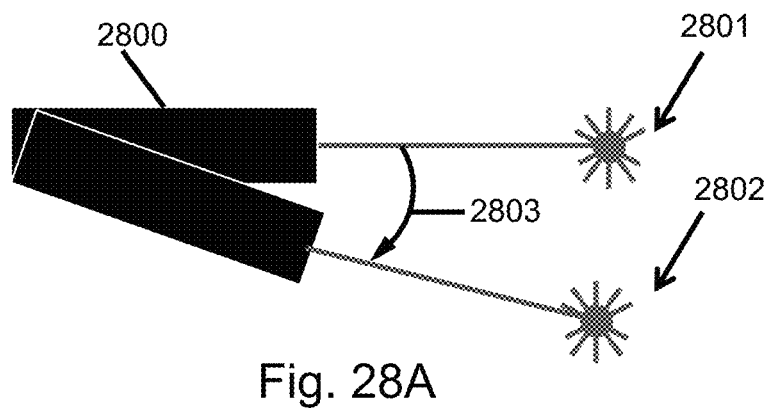
FIG. 28A is a side view illustration of Laser Range Finder (aka, lidar).

FIG. 28A illustrates a side view of the adjustable vertical angle of the lidar system. 2800 illustrates the lidar. 2801 illustrates the laser beam at a first vertical position. 2802 illustrates the laser beam at a second vertical position. 2803 illustrates the adjustable angle, which is at least 30 degrees of vertical angle adjustment. Thus, the vertical angle adjustment can account for a person's height and posture while performing activities, such as walking or surgery.

Figure 28B:
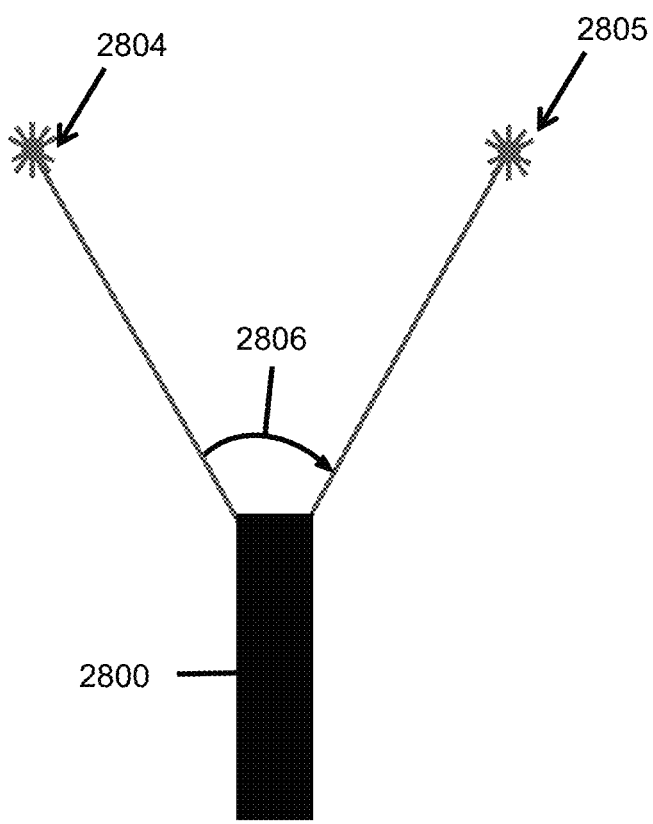
FIG. 28B is a top-down view illustration of Laser Range Finder (aka, lidar).

FIG. 28B illustrates a top-down view of the lidar system. 2800 illustrates the lidar. 2804 illustrates the laser beam at a first horizontal position. 2805 illustrates the laser beam at a second horizontal position. 2806 illustrates the adjustable angle, which is at least 45 degrees of horizontal angle adjustment. The scan pattern varies based on the task that the user is accomplishing.

Figure 29:
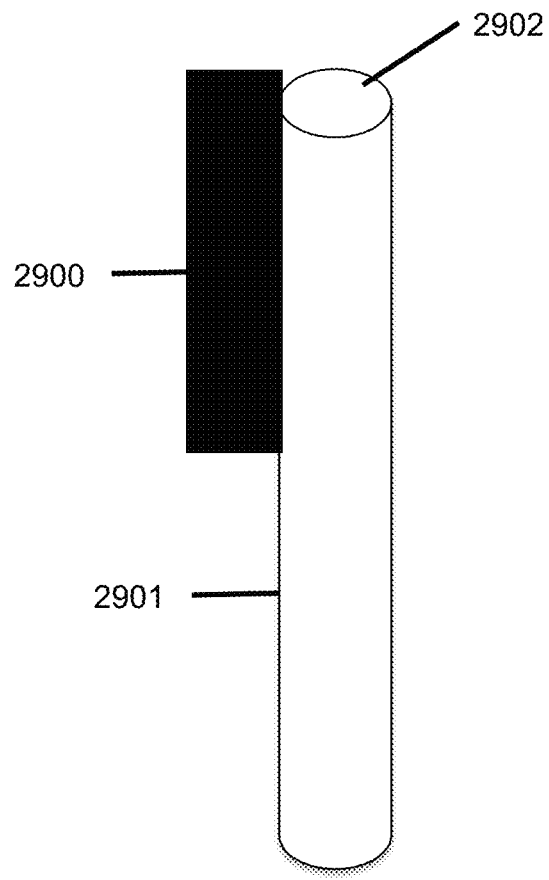
FIG. 29 is an illustration of the laser range finder on an endoscopy device.

FIG. 29 illustrates an endoscopy probe, which is equipped with a lidar range finding system. This system is called endoscopic lidar. Such 2900 illustrates the lidar system. 2901 illustrates a portion of the endoscopy probe. 2902 illustrates the camera at the end of the endoscopy probe. Note that this can be used to generating a real time depth map of the internal cavity (e.g., peritoneal cavity). Laser scanning with lidar can be used to generate 3D datasets comprised of voxels. Such datasets can be registered to conventional radiological imaging datasets (e.g., CT, MRI, etc.). The lidar that is preferred is the infrared spectrum because this can see through smoke commonly present during cauterization during endoscopy. This endoscopic lidar system can have a vertical angle scanning pattern and a horizontal angle scanning pattern. A dual system can be used by the surgeon. First, the surgeon can use the visible light camera to approach a lesion that needs to be cauterized. Then, the surgeon cauterizes a lesion. Then, the smoke appears and the surgeon then has poor visualization of the scene. The surgeon then switches to the endoscopic lidar system and the real time lidar system is performed. The display can be the 2D monitor or the extended reality glasses. The surgeon can then see the details of the scene and perform image processing of the voxelated dataset and continue to operate based on the new data. This is useful because it can eliminate dead time and speed up the surgical procedure. Some embodiments comprise wherein the lidar sensor generates a voxelated dataset from the inside of a patient's body during endoscopic surgery. For example, the lidar sensor could generate a voxelated dataset of the inside of the trachea during a bronchoscopy examination. Some embodiments comprise wherein the voxelated lidar dataset is registered to a cross-sectional imaging examination voxelated dataset. For example, the voxelated dataset of the inside of the trachea during a bronchoscopy examination can be registered to the trachea from a voxelated dataset from a chest CT examination. Some embodiments comprise wherein a surgeon uses the co-registered voxelated dataset for surgical navigation. For example, a tumor could be marked on the CT scan and the real time voxelated dataset from the lidar sensor co-registered to the CT scan could be used as navigation. For example, the distance to the tumor could be marked.

Figure 30A:
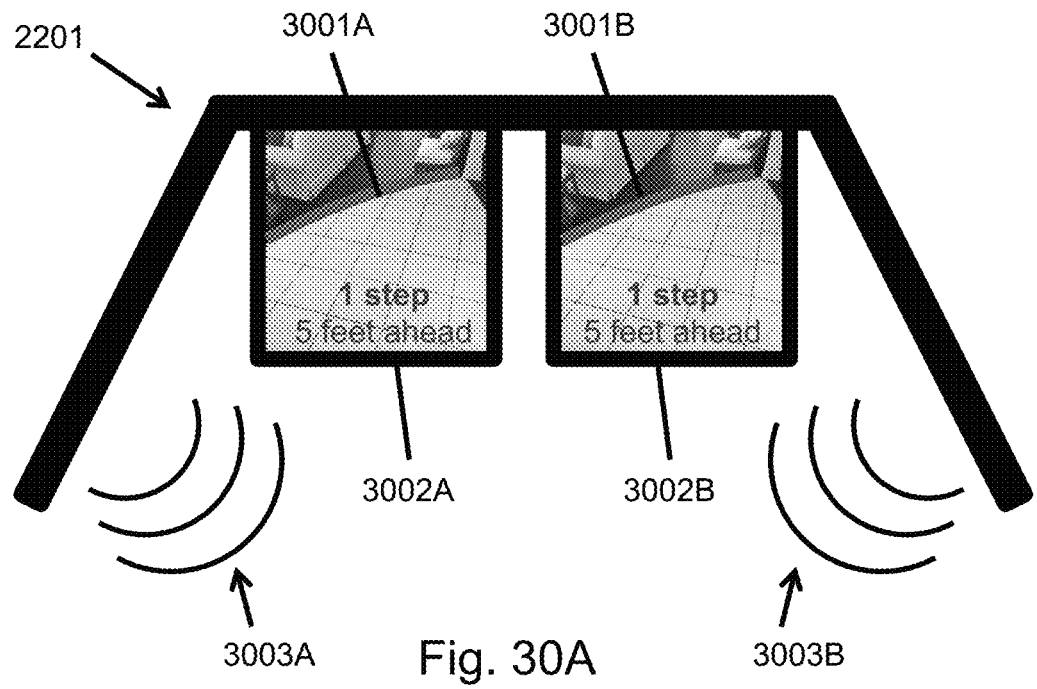
FIG. 30A illustrates an augmented reality/mixed reality headset and what a person sees in the headset in a first set of conditions.

FIG. 30A illustrates the SGS 2201 and what a person sees in the headset in a first set of conditions. The real scene can be seen by the user through the transparent lenses. A computer generated line 3001A is illustrated on the left eye display to assist the user in identifying an obstacle, such as a step. A computer generated line 3001B is illustrated on the right eye display to assist the user in identifying an obstacle, such as a step. This serves to help a user visualize an obstacle that might be poorly visualized. Text 3002A, which states "1 step 5 feet ahead" is illustrated on the left eye display to alert the user of details regarding the obstacle. Text 3002B, which states "1 step 5 feet ahead" is illustrated on the right eye display to alert the user of details regarding the obstacle. The headset 3000 can have an audio notification 3003A from the left sided speakers to alert the user of the obstacle, such as a voice that states "1 step down 5 feet ahead." The headset 3000 can have an audio notification 3003B from the right sided speakers to alert the user of the obstacle, such as a voice that states "1 step down 5 feet ahead."

Figure 30B:
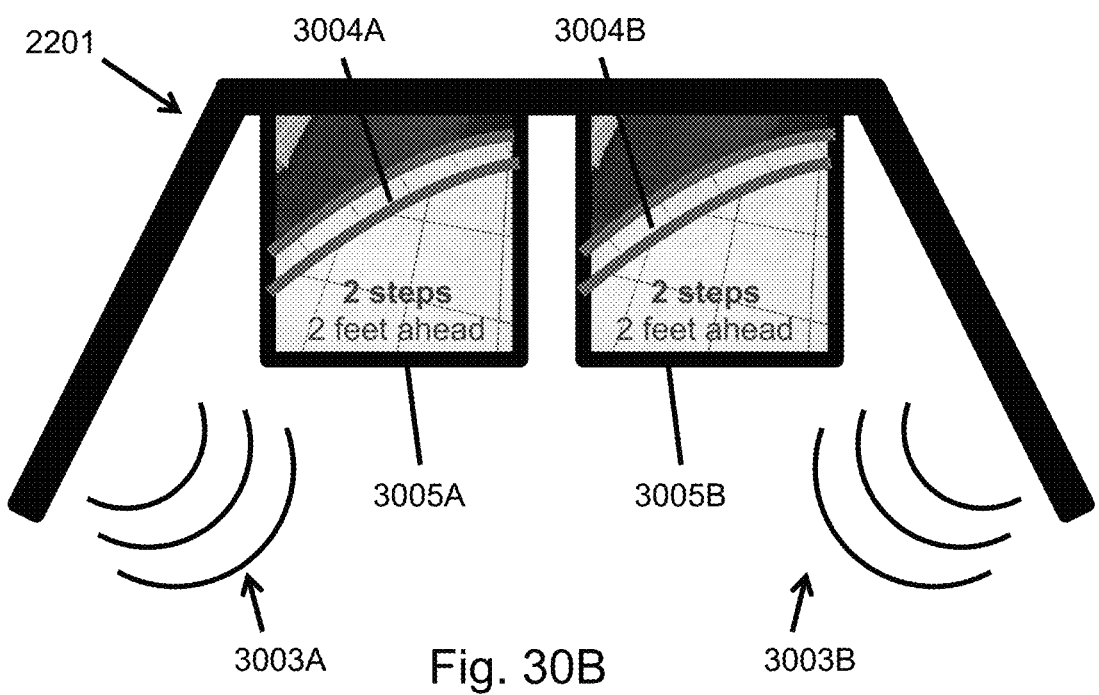
FIG. 30B illustrates an augmented reality/mixed reality headset 3000 and what a person sees in the headset in a second set of conditions.

FIG. 30B illustrates the SGS 2201 and what a person sees in the headset in a second set of conditions. The real scene can be seen by the user through the transparent lenses. A computer generated lines 3004A are illustrated on the left eye display to assist the user in identifying an obstacle, such as steps downward. A computer generated lines 3004B are illustrated on the right eye display to assist the user in identifying an obstacle, such as steps downward. This serves to help a user visualize an obstacle that might be poorly visualized (e.g., low contrast between the two steps). Text 3005A which states "2 steps 2 feet ahead" is illustrated on the left eye display to alert the user of details regarding the obstacle. Text 3005B which states "2 steps 2 feet ahead" is illustrated on the right eye display to alert the user of details regarding the obstacle. The headset 3000 can have an audio notification 3006B to alert the user of the obstacle, such as a voice that states "2 steps down 2 feet ahead" coming from left sided speakers. The headset 3000 can have an audio notification 3006B to alert the user of the obstacle, such as a voice that states "2 steps down 2 feet ahead" coming from left sided speakers. This example is of a warning condition regarding the condition of an irregular ground surface.

Figure 31A:
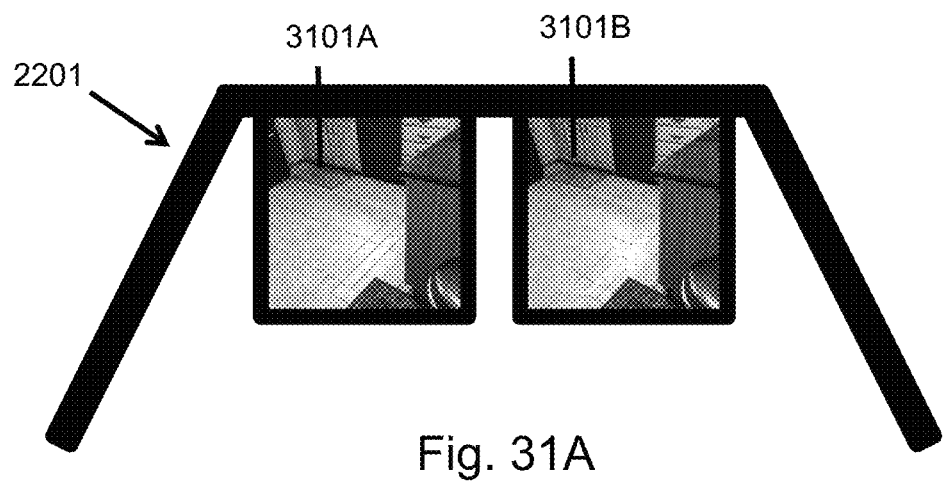
FIG. 31A illustrates a first location at a first time point.

FIG. 31A illustrates a first location at a first time point. For example, a reference scene reflects what is a 'normal' condition which is free of obstacles that might cause one to trip, etc. A user could walk around their home and familiar places and the headset can learn the surroundings by storing data from the Laser Range Finder (LRF), Low Light Level TV and FLIR cameras. The SGS 2201 is shown. The left eye view first location at a first time point 3101A is shown. The right eye view first location at a first time point 3101B is shown.

Figure 31B:
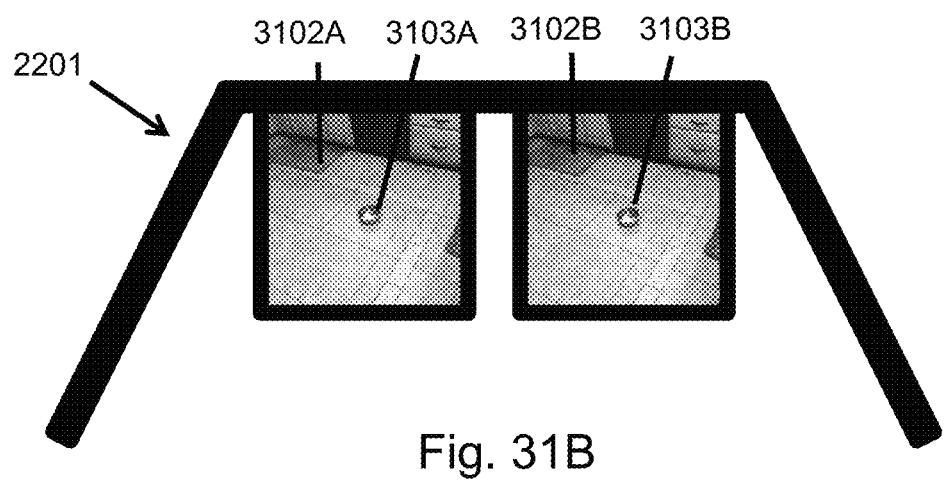
FIG. 31B illustrates the first location at a second time point.

FIG. 31B illustrates the first location at a second time point. For example, this second scene reflects a condition wherein something (e.g., a dog dish) is along the path from the kitchen door to the sink. The user can walk around their home and a new set of data from the Laser Range Finder (LRF), Low Light Level TV and FLIR cameras can be stored. The SGS 2201 is shown. The left eye view of the first location at a second time point 3102A is shown. The right eye view of the first location at a second time point 3102B is shown. A left eye view of a new object 3103A is in the scene. A right eye view of a new object 3103B is in the scene.

Figure 31C:
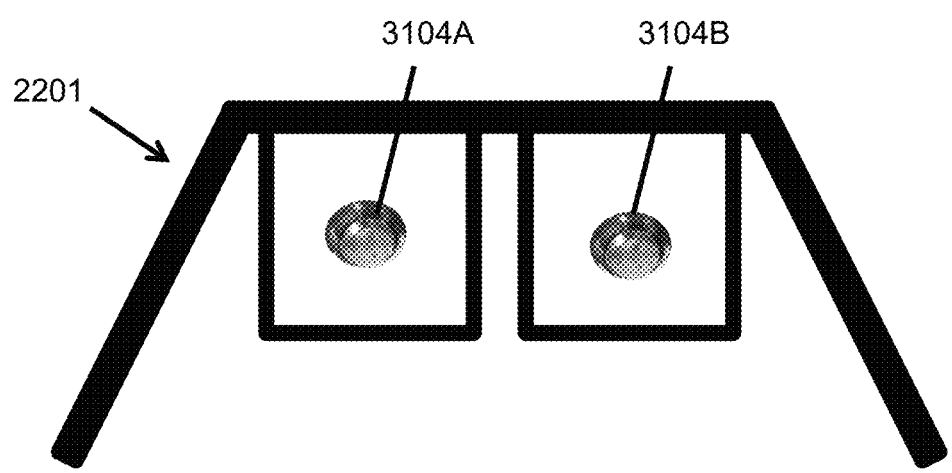
FIG. 31C illustrates interval change at the first location between the first time point and the second time point.

FIG. 31C illustrates interval change at the first location between the first time point and the second time point. The SGS can determine differences between the first time point and the second time point by performing scene subtraction from the Laser Range Finder (LRF), Low Light Level TV and FLIR cameras at the first time point as compared to the second time point. This shows the person wearing the SGS the obstacle in path. The obstacle can be enlarged 3104A and shown on the left eye display. The obstacle can be enlarged 3104B and shown on the right eye display. Arrow annotations or other alert methods can also be used to notify the user of the new obstacle.

Figure 32A:
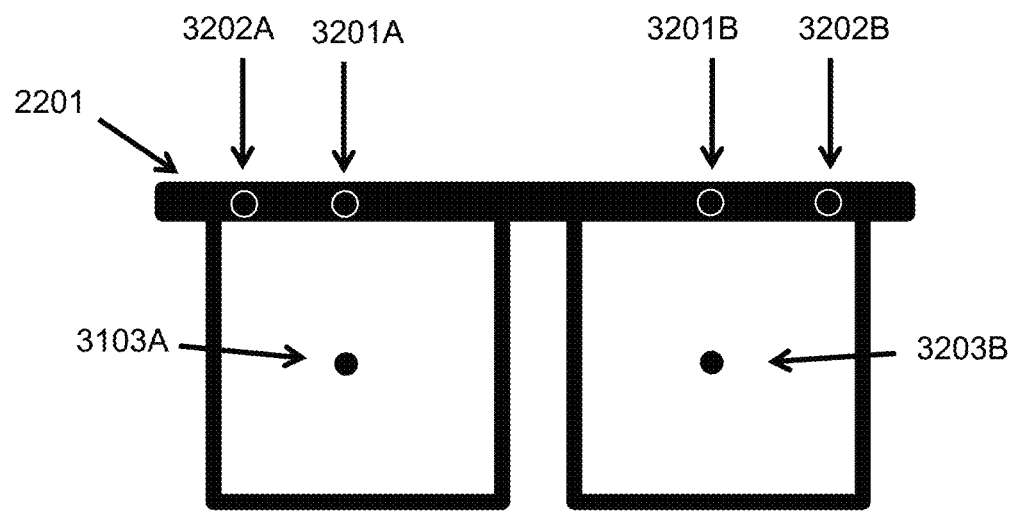
FIG. 32A illustrates example fixed positions for the low light level TV (L3TV) camera.

FIG. 32A illustrates a front view of the SGS 2201 and the low light level TV (L3TV) camera, in a fixed location. In order to have stereoscopic vision which corresponds to the way the brain has been taught to work, two L3TV cameras are utilized. The L3TV cameras could be placed in above, below, to the medial side or to the lateral side of the eyes. The example location for the L3TV cameras above the right eye location 3201A is shown. The example location for the L3TV cameras above and to the lateral aspect of the right eye 3202A is shown. The example location for the L3TV cameras directly in front of the right eye 3203A is shown and could do so with minimal interference if the camera was small. The example location for the L3TV cameras above the left eye location 3201B is shown. The example location for the L3TV cameras above and to the lateral aspect of the left eye 3202B is shown. The example location for the L3TV cameras directly in front of the left eye 3203B is shown and could do so with minimal interference if the camera was small. From this position, the person wearing the SGS would receive true stereoscopic imagery presented in a manner the brain is accustomed to. The see-through capability of the SGS would be partially occluded.

Figure 32B:
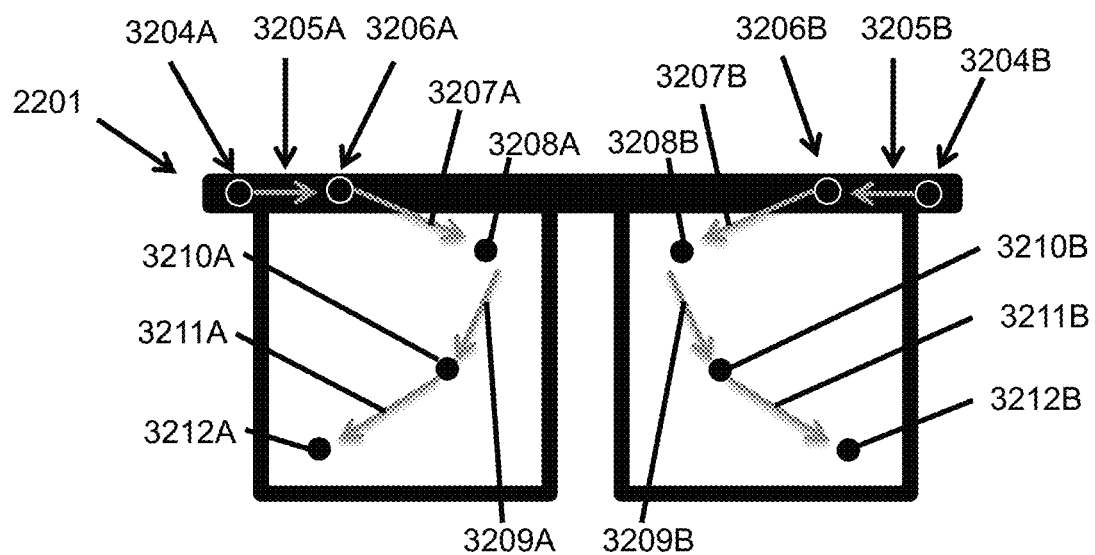
FIG. 32B illustrates example movable positions for the low light level TV (L3TV) camera.

FIG. 32B illustrates a front view of the SGS 2201 and the low light level TV (L3TV) camera with a movable location. It may be preferable to the person wearing the SGS change the L3TV camera location. This would enable the person wearing the SGS to both see through the lenses without occlusion and also have the camera display albeit not exactly the exact same stereoscopic view that one's brain is accustomed to. 3200 illustrates the SGS. 3204A illustrates a first position of the right eye L3TV camera, which is superior and lateral to the right eye. 3205A illustrates movement from the first position of the right eye L3TV camera 3204A to the second position of the right eye L3TV camera 3206A, which is directly above the right eye. 3207A illustrates movement from the second position of the right eye L3TV camera 3206A to the third position of the right eye L3TV camera 3208A, which is superior and medial to the right eye. 3209A illustrates movement from the third position of the right eye L3TV camera 3208A to the fourth position of the right eye L3TV camera 3210A, which is medial to the right eye. 3211A illustrates movement from the fourth position of the right eye L3TV camera 3210A to the fifth position of the right eye L3TV camera 3212A, which is inferior and lateral to the right eye. 3204B illustrates a first position of the left eye L3TV camera, which is superior and lateral to the left eye. 3205B illustrates movement from the first position of the left eye L3TV camera 3204B to the second position of the left eye L3TV camera 3206B, which is directly above the left eye. 3207B illustrates movement from the second position of the left eye L3TV camera 3206B to the third position of the left eye L3TV camera 3208B, which is superior and medial to the left eye. 3209B illustrates movement from the third position of the left eye L3TV camera 3208B to the fourth position of the left eye L3TV camera 3210B, which is medial to the left eye. 3211B illustrates movement from the fourth position of the left eye L3TV camera 3210B to the fifth position of the left eye L3TV camera 3212B, which is inferior and lateral to the right eye. The key advantage is adjustment of stereopsis for different users, since different people have different interocular distances.

Figure 33A:
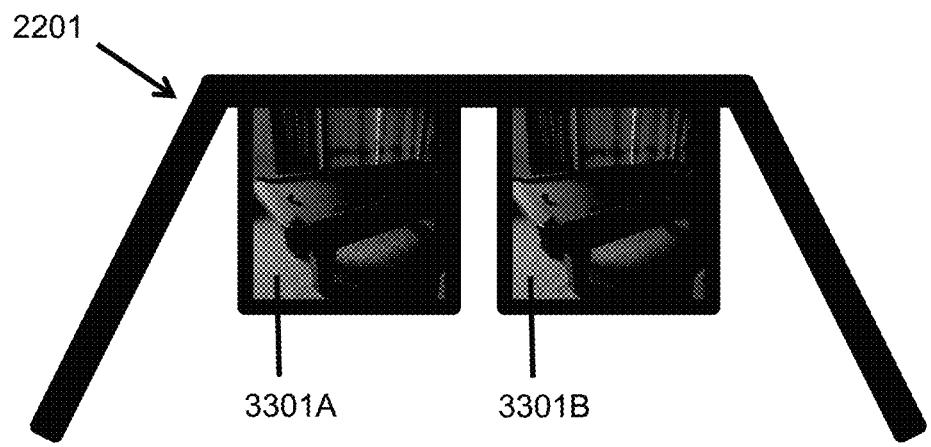
FIG. 33A illustrates what picture a person sees when the L3TV camera is off.

FIG. 33A illustrates what a person sees through the SGS with the L3TV camera turned off. 2201 is the SGS. 3301A is what the user sees when looking through the left eye display. 3301B is what the user sees when looking through the right eye display.

Figure 33B:
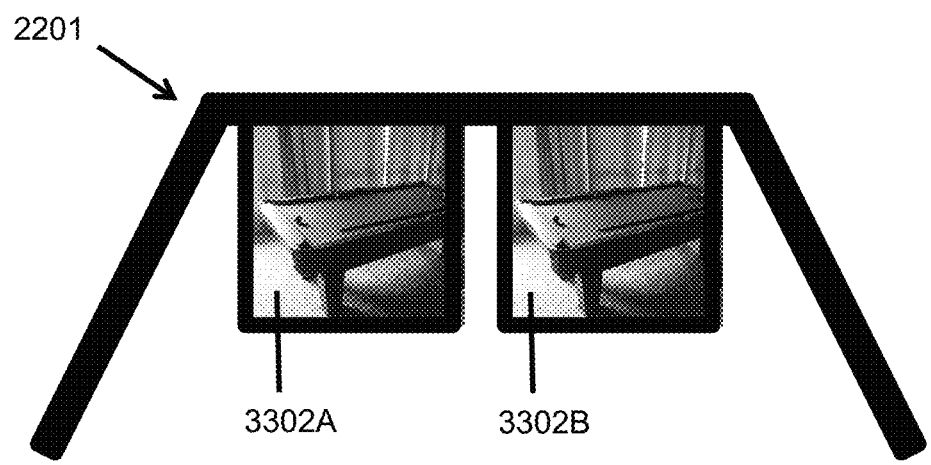

FIG. 33B illustrates what a person sees through the SGS with the L3TV camera turned on. 2201 is the SGS. 3302A is what the user sees when looking through the left eye display, which is a brighter image as compared to 3301A due to enhancements from the L3TV camera. 3302B is what the user sees when looking through the right eye display, which is a brighter image as compared to 3301B due to enhancements from the L3TV camera. When the person wearing the SGS utilizes the L3TV camera mode, the room appears as it normally would in daytime in grayscale.

Figure 34A:
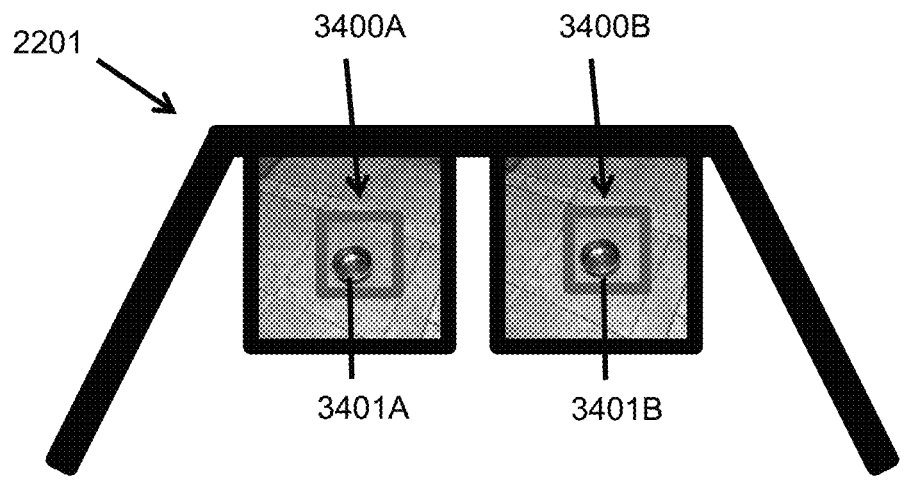
FIG. 34A illustrates an example obstacle on the floor.

FIG. 34A illustrates an obstacle seen in the SGS. A person may want to see the obstacle in greater detail and can use the implement the "zoom" function of the SGS. The zoom function could be accomplished by digital zoom or optical zoom of a forward looking camera. The direction of the forward looking camera can match that of the user's gaze direction. The eye facing cameras are used to determine gaze direction (e.g., 10 degrees upward from the horizontal and 10 degrees to the left) and the zoom function can be performed at that same location (e.g., 10 degrees upward from the horizontal and 10 degrees to the left). In addition, storage of video stream can be utilized, so that replays can be performed including the rewind, fast forward, slow motion, and pause functions. Object tracking can also be implemented through the SGS camera system. For example, this can help the user better track the trajectory of a golf ball. The user can issue the voice command of "zoom in" to zoom in and "zoom out" to zoom out. Alternatively gesture tracking can also be performed to control zooming. For example, a user can move one's hand or finger to overlie a particular spot in the distance and then implement the zoom command. A user can use a region of interest marker around an object and then zoom in on that region. The region of interest marker can vary in shape, color, size and type of line. Alternatively, crosshairs placed on the object of interest can be utilized. A red box region of interest for the left eye display 3400A of the SGS 2201 is shown. A red box region of interest for the right eye display 3400B of the SGS 2201 is shown. The obstacle can be seen through the left eye display 3401A of the SGS 2201. The obstacle can be seen through the right eye display 3401B of the SGS.

Figure 34B:
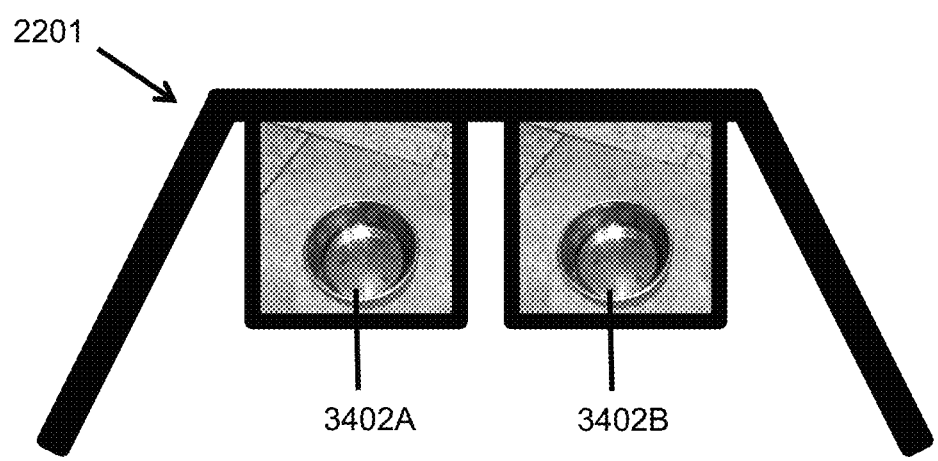
FIG. 34B illustrates what a person sees when person invokes 'zoom' function while using L3TV camera.

FIG. 34B illustrates the what the user would see after the zoom function is implemented. Note that the camera horizontal and vertical fields-of-view (FOV) would be reduced by a preselected amount and the display would change accordingly. The zoom command could be involved multiple time at the discretion of the person wearing the SGS. The obstacle can be seen through the left eye display 3402A in a zoomed in fashion. The obstacle can be seen through the right eye display 3402B in a zoomed in fashion. Note that the field of view in the left eye display corresponds to the region of interest marker 3400A and the field of view in the right eye display corresponds to the region of interest marker 3400B. This could be useful for the elderly who would might need assistance in reading small font. For example, the SGS could learn the location of the page based on the user's region of interest marker, perform optical character recognition and then display the words in the SGS per user preference including changing font size, font style and background color. Thus, the SGS can be used as a reading assistance device.

Figure 35A:
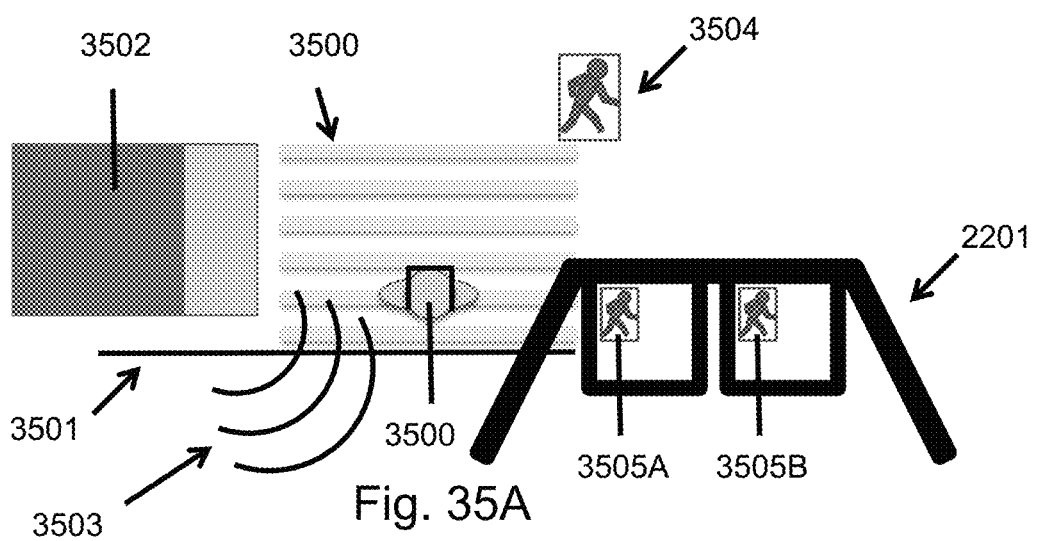
FIG. 35A illustrates a car in a stopped position and the walk signal on the street.

FIG. 35A illustrates a first scenario at a crosswalk. 3500 is a crosswalk. 3501 is a curb. 3502 is a car in a stopped position. 3503 is the sound of the engine of the car 3502.

3504 is a cross-walk sign indicating walk. 2201 is the SGS. 3505A is the walk sign indicator in the left eye display of the SGS 2201. 3505B is the walk sign indicator in the right eye display of the SGS 2201. The user 3506 sees the actual walk sign 3504 on the street as a real world image through the SGS and the walk sign indicators 3505A and 3505B displayed as virtual image in the SGS and is walking across the crosswalk. Note that in this scenario both the actual image and virtual image are in agreement indicating walk.

Figure 35B:
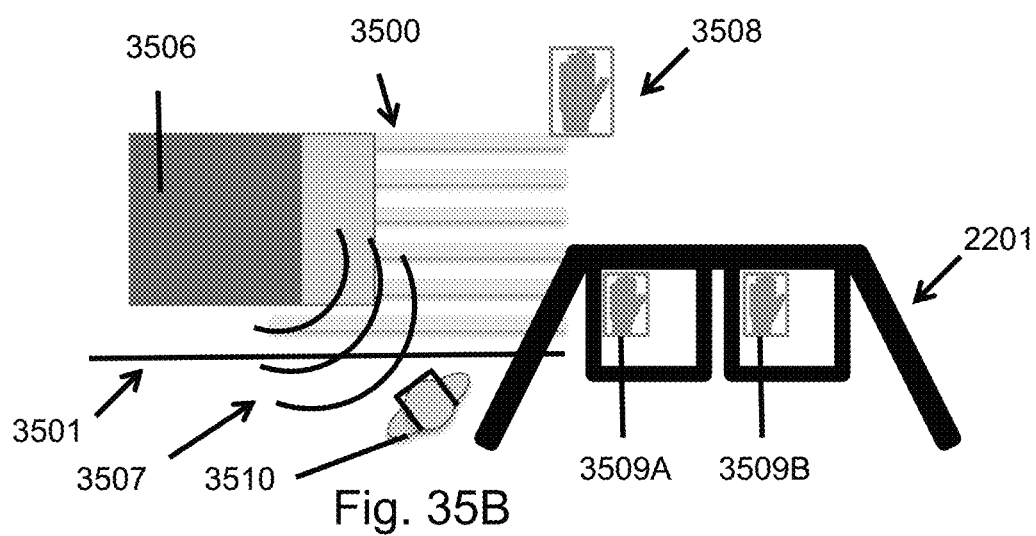
FIG. 35B illustrates a car in a stopped position and the stop signal on the street.

FIG. 35B illustrates a second scenario at a crosswalk. 3500 is a crosswalk. 3501 is a curb. 3506 is a car moving relative to the crosswalk 3500. 3507 is the sound of the approaching car 3506. 3508 is a cross-walk sign indicating stop. 2201 is the SGS. 3509A is the stop indicator in the left eye display of the SGS 2201. 3509B is the stop indicator in the right eye display of the SGS 2201. The user 3510 sees the actual cross-walk sign 3508 indicating stop on the street as a real world image through the SGS and the stop indicators 3509A and 3509B displayed as virtual image in the SGS and is walking across the crosswalk. The user 3510 is stopped and waiting safely on the curb 3501. Note that in this scenario both the actual image and virtual image are in agreement indicating stop.

Figure 35C:
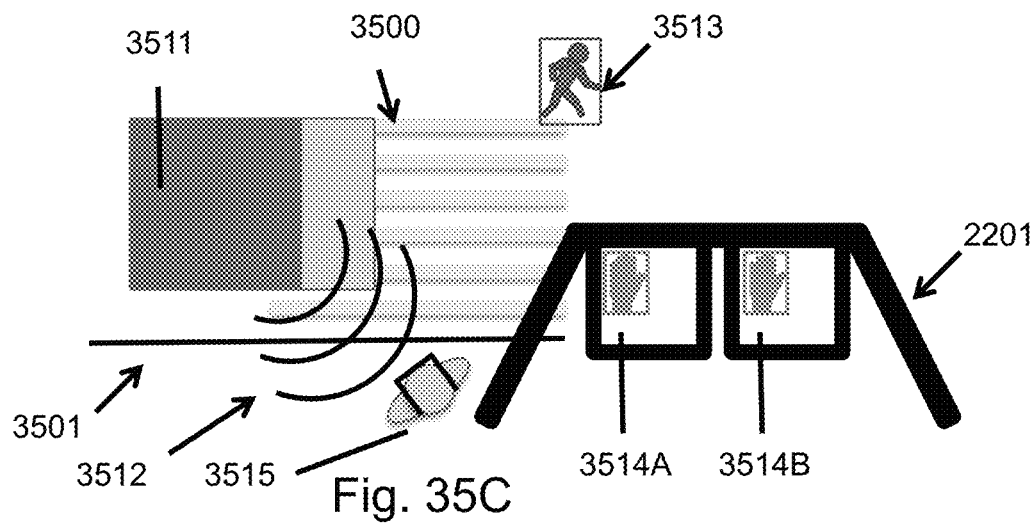
FIG. 35C illustrates a car in a stopped position and the walk signal on the street.

FIG. 35C illustrates a third scenario at a crosswalk. 3500 is a crosswalk. 3501 is a curb. 3511 is a car moving relative to the crosswalk 3500. 3512 is the sound of the approaching car 3511. 3513 is a cross-walk sign indicating walk. 2201 is the SGS. 3514A is the stop indicator in the left eye display of the SGS 2201. 3514B is the stop indicator in the right eye display of the SGS 2201. The user 3515 sees the actual cross-walk sign 3513 indicating walk on the street as a real world image through the SGS and the stop indicators 3514A and 3514B displayed as virtual image in the SGS and is walking across the crosswalk. The user 3510 is stopped and waiting safely on the curb 3501. Note that in this scenario the actual image and virtual image are in disagreement. The user can be trained to trust the SGS and heed the additional warning. In this scenario, the car 3511 is running a red light and the SGS 2201 alerts the user to stop and wait safely at the curb. The SGS can be programmed to automatically alert the user to preselected imaging findings or sounds. For example, the walk sign could be a preselected imaging finding that is automatically detected by the SGS and displayed to the user via audio and/or visual notification in an enlarged alert box to the user as a pop-up. For example, the sound of an incoming car can be a preselected sound that is automatically detected by the SGS and displayed to the user via audio and/or visual notification. This figure illustrates enhancement of situational awareness capability of SGS. The person wearing the SGS would issue a voice command such as "SA on". At that juncture the compute component would run, for example, detection algorithms for approaching/receding/stationary vehicles. Given a vehicle were approaching, a warning message would be generated and a symbol (e.g., arrow) displayed to point the direction of the approaching vehicle. If the person wearing the SGS turned toward the vehicle and placed the crosshair on it, the LRF could pass to the computer range to the vehicle at multiple time intervals. From that, the computer would compute range rate (i.e., speed of vehicle) and time to close with the person wearing the SGS. If the person wearing the SGS were at a crosswalk at a road intersection, the acoustics element would be in communication with the computer element which could detect a change in vehicle status. For example, the sounds emitted from a vehicle being stationary to accelerating after being stopped at a traffic light to approaching as the vehicle turned to go over the crosswalk. Such a situation could present a danger to the person wearing the SGS. The person wearing the SGS, might want to know when it would be safe to proceed and look to the pedestrian light signal and invoke the zoom command to obtain a better picture of the signal status (e.g., walk/time remaining/wait). Example sequences of events follows.

FIG. 36 illustrates a flow diagram wherein the user is alerted of an adverse scenario. Step 3600 is to generate a predetermined list of adverse event scenarios. Step 3601 is to establish a set of criteria for each sensor system that is predictive of an adverse event scenario. Step 3602 is to perform continuous analysis of the data gathered from the sensors on the HDU to determine if the set of criteria for each sensor system that is predictive of an adverse event scenario is met. Step 3603 is when the set of criteria for each sensor system that is predictive of an adverse event scenario is met provide an alert to the user via at least one of the group of: a visual alert wherein the HDU causes a first image of a volume of interest to be displayed on the left eye display and cause a second image of the volume of interest to be displayed on the right eye display, wherein the first image is aligned with a left eye of a user, and wherein the second image is aligned with a right eye of the user; and an audio alert from the set of speakers. For example, the adverse event scenarios includes a dangerous physical examination finding of a patient. It can be difficult for a physician to notice all aspects of a patient's physical examination. For example, a physician may be talking to a patient with a melanoma on the back of his hand for 10 minutes, but not notice it. The patient may fail to report it to the doctor. Therefore, it is possible that a dangerous skin lesion go unreported. Other findings include movement analysis, respiratory rate, sclera color, bruise, posture or other type of physical examination findings. A database of adverse physical examination findings can be compiled. Then, artificial intelligence can compare the real time video stream with the database. If physical examination finding is thought (by the artificial intelligence algorithm) to represent a dangerous physical examination finding, then the physician can be alerted. For example, the adverse event scenarios includes a dangerous observation during surgery. For example, active bleeding may be present during the surgery, but go unnoticed during surgery. Other examples include dislodged surgical device, foreign body detection, tumor implants, and others. A database of adverse surgical findings can be compiled. Then, artificial intelligence can compare the real time video stream with the database. If the surgical finding is thought (by the artificial intelligence algorithm) to represent a dangerous surgical finding, then the surgeon can be alerted. For example, the adverse event scenarios includes a dangerous event during driving. For example, a pedestrian may be crossing the highway in front of fast moving traffic. Alternatively, a driver may be drifting off to sleep and the driver's head falls downward. Alternatively, the driver may be driving over the lane markers. A database of adverse findings (and associated sensor data) when driving can be compiled. Then, artificial intelligence can compare the real time video stream with the database. If a driving finding is thought (by the artificial intelligence algorithm) to represent a dangerous driving scenario, then the driver can be alerted (e.g., via audio or visual feedback from the HDU). For example, the adverse event scenario includes dangerous events during walking. For example, a user may be crossing the crosswalk when the walk sign is on, but a car could be running the red light. A database of adverse findings (and associated sensor data) when walking can be compiled. The findings can be trip hazards. Then, artificial intelligence can compare the real time video stream with the database. If a walking finding is thought (by the artificial intelligence algorithm) to represent a dangerous walking scenario, then the walker can be alerted (e.g., via audio or visual feedback from the HDU). For example, the adverse event scenario includes dangerous events that can occur in the household. For example, a user may be cooking, but forget to turn off the stove. Alternatively, the user may be prescribed to walk every hour by their to avoid blood clots, but forget to get up and walk. A database of adverse findings (and associated sensor data) when doing household activities can be compiled. Then, artificial intelligence can compare the real time video stream with the database. If a household finding is thought (by the artificial intelligence algorithm) to represent a dangerous walking scenario, then the walker can be alerted (e.g., via audio or visual feedback from the HDU). For example, the adverse event scenario includes dangerous events that can occur in sports. For example, a user may be about to take a golf shot near a tree root, which could interfere with a swing. A database of adverse findings (and associated sensor data) when doing sports activities can be compiled. Then, artificial intelligence can compare the real time video stream with the database. If a sports finding is thought (by the artificial intelligence algorithm) to represent a dangerous scenario, then the player can be alerted (e.g., via audio or visual feedback from the HDU). For example, the adverse event scenario includes dangerous events that can occur in occupations. For example, a user may be about to perform work on an electrical box and about to touch a live wire. Alternatively, it could be a plumber working under the sink looking for a leak. A database of adverse findings (and associated sensor data) when doing various occupations can be compiled. Then, artificial intelligence can compare the real time video stream with the database. If an occupation finding is thought (by the artificial intelligence algorithm) to represent a dangerous scenario, then the worker can be alerted (e.g., via audio or visual feedback from the HDU).

FIG. 37 illustrates a flow diagram for a method to alert a user of a hazardous scenario. Step 3700 is a to generate a predetermined list of adverse event scenarios. Step 3701 is to generate a database of sensor data of scenarios known to be adverse. Step 3702 is to generate a database of sensor data of scenarios known not to be adverse. Step 3703 is to gather sensor data from a head display unit (HDU). Step 3704 is to perform artificial intelligence in real time to classify the sensor data as predictive of an adverse event scenario or not predictive of an adverse event scenario. Step 3705 is to alert a user wearing the HDU when the artificial intelligence algorithm predicts an adverse event scenario by a predetermined alert notification via at least one of the group of: a visual alert notification wherein the HDU causes a first image to be displayed on the left eye display and cause a second image of the volume of interest to be displayed on the right eye display, wherein the first image is aligned with a left eye of a user, and wherein the second image is aligned with a right eye of the user wherein the visual alert notification corresponds to the specific adverse event scenario; and an audio alert notification from at least one speaker wherein the auditory alert notification corresponds to the specific adverse event scenario.

FIG. 38 illustrates a table of programmed visual alert notifications and auditory alert notifications to correspond to adverse event scenarios. The table is self explanatory. Several features, aspects, embodiments and implementations have been described.

Nevertheless, it will be understood that a wide variety of modifications and combinations may be made without departing from the scope of the inventive concepts described herein. Accordingly, those modifications and combinations are within the scope of the following claims.

What is claimed is:

1. A head display unit (HDU) comprising:
   a processor;
   a head tracking device configured to track movements of a user's head;
   a lidar device configured to scan an area wherein said lidar device has an adjustable vertical angle and an adjustable horizontal angle;
   a left eye display operably connected to the processor;
   a right eye display operably connected to the processor;
   a non-transitory memory having computer-executable instructions stored thereupon which, when executed by the processor of the head display unit, cause the HDU to:
      use said lidar device to perform scanning of said area
         wherein data from said perform scanning of said area by said lidar device is used to generate a 3D dataset, and
         wherein said 3D dataset represents said area;
      generate a 3D representation of said 3D dataset wherein said 3D representation is superimposed on said area; and
      display said 3D representation stereoscopically to said user
         wherein said HDU causes a first image of said 3D representation to be displayed on said left eye display and causes a second image of said 3D representation to be displayed on said right eye display,
         wherein said first image is aligned with a left eye of said user, and
         wherein the second image is aligned with a right eye of said user.

2. The HDU of claim 1 further comprising determining if an adverse event scenario is present.

3. The HDU of claim 2 further comprising wherein the adverse event scenario includes a dangerous observation during surgery.

4. The HDU of claim 2 further comprising wherein the adverse event scenario includes a dangerous observation during driving.

5. The HDU of claim 2 further comprising wherein the adverse event scenario includes a dangerous event when walking.

6. The HDU of claim 2 further comprising wherein the adverse event scenario includes a household scenario.

7. The HDU of claim 2 further comprising wherein the adverse event scenario includes a sports scenario.

8. The HDU of claim 2 further comprising wherein the adverse event scenario includes an occupation scenario.

9. A method of alerting a user of a hazardous scenario comprising:
   generating a database comprising:
      a list of adverse event scenarios; and
      finding(s) corresponding to each adverse event scenario in said list of adverse event scenarios;
   performing scanning of area using a lidar device,
      wherein said lidar device is located on a head display unit (HDU),
      wherein said lidar device has an adjustable vertical angle and an adjustable horizontal angle, and
      wherein data from said performing scanning of said area using said lidar device is used to generate a 3D dataset, performing an analysis of said 3D dataset to determine if said 3D dataset contains finding(s) predictive of an adverse event scenario in said list of adverse event scenarios; and if said analysis predicts an adverse event scenario, alerting said user wearing said HDU by at least one of the group consisting of:
- a visual alert notification wherein said HDU causes a first image to be displayed on a left eye display of said HDU and causes a second image to be displayed on a right eye display of said HDU
  - wherein the first image is aligned with a left eye of said user, and
  - wherein the second image is aligned with a right eye of said user; and
- an audio alert notification from at least one speaker.

10. The method of claim 9 further comprising wherein the adverse event scenario includes a dangerous physical examination finding of a patient.

11. The method of claim 9 further comprising wherein the adverse event scenario includes a dangerous observation during surgery.

12. The method of claim 9 further comprising wherein the adverse event scenario includes a dangerous observation during driving.

13. The method of claim 9 further comprising wherein the adverse event scenario includes a dangerous event when walking.

14. The method of claim 9 further comprising wherein the adverse event scenario includes a household scenario.

15. The method of claim 9 further comprising wherein the adverse event scenario includes a sports scenario.

16. The method of claim 9 further comprising wherein the adverse event scenario includes an occupation scenario.

* * * * *